(12) United States Patent
Troy et al.

(10) Patent No.: US 10,945,658 B2
(45) Date of Patent: Mar. 16, 2021

(54) SYSTEMS AND METHODS FOR EARLY DETECTION OF FRACTURE HEALING

(71) Applicants: Worcester Polytechnic Institute, Worcester, MA (US); Beth Israel Deaconess Medical Center, Inc., Boston, MA (US)

(72) Inventors: Karen L. Troy, Worcester, MA (US); John J. Wixted, Boston, MA (US); Ara Nazarian, Boston, MA (US)

(73) Assignees: Worcester Polytechnic Institute, Worcester, MA (US); Beth Israel Deaconess Medical Center, Inc., Boston, MA (US)

( * ) Notice: Subject to any disclaimer, the term of this patent is extended or adjusted under 35 U.S.C. 154(b) by 299 days.

(21) Appl. No.: 15/956,830

(22) Filed: Apr. 19, 2018

(65) Prior Publication Data
US 2018/0303408 A1    Oct. 25, 2018

Related U.S. Application Data

(60) Provisional application No. 62/487,190, filed on Apr. 19, 2017.

(51) Int. Cl.
*A61B 5/00* (2006.01)
*A61B 6/00* (2006.01)
(Continued)

(52) U.S. Cl.
CPC .......... *A61B 5/4504* (2013.01); *A61B 5/0053* (2013.01); *A61B 5/0555* (2013.01); *A61B 5/1036* (2013.01); *A61B 5/7275* (2013.01); *A61B 6/032* (2013.01); *A61B 6/505* (2013.01); *A61B 5/1495* (2013.01); *A61B 5/6824* (2013.01); *G01N 2800/10* (2013.01); *G06T 7/0012* (2013.01); *G06T 2207/30008* (2013.01)

(58) Field of Classification Search
CPC ... A61B 5/0053; A61B 5/0555; A61B 5/1036; A61B 5/4504; A61B 5/7275; A61B 17/7053; A61B 2002/4666; A61B 6/032; A61B 6/505

See application file for complete search history.

(56) References Cited

U.S. PATENT DOCUMENTS

| 5,697,165 A | 12/1997 | Richardson |
| 5,810,750 A | 9/1998 | Buser |

(Continued)

OTHER PUBLICATIONS

International Search Report in PCT International Application No. PCT/US2018/028251 dated Jun. 26, 2018.

*Primary Examiner* — Max F Hindenburg
(74) *Attorney, Agent, or Firm* — Greenberg Traurig, LLP; Roman Fayerberg

(57) ABSTRACT

In some embodiments, there is provide a method of analysing a bone fracture, comprising; stabilizing a bone having a fracture including a first support point located distal of the fracture and a second support point located proximal of the fracture; applying a force to an area of the bone having the fracture to cause a displacement of the fracture; imaging the bone during the application of force thereto; and comparing the image of the bone during the application of force to an image of the bone without the application of force to determine the state of the fracture.

6 Claims, 35 Drawing Sheets

(51) Int. Cl.
*A61B 6/03* (2006.01)
*A61B 5/103* (2006.01)
*A61B 5/055* (2006.01)
*G06T 7/00* (2017.01)
*A61B 5/1495* (2006.01)

(56) References Cited

U.S. PATENT DOCUMENTS

| | | | |
|---|---|---|---|
| 8,687,865 | B2 | 4/2014 | Wilson et al. |
| 10,582,932 | B2 * | 3/2020 | Shaker ................. A61B 17/132 |
| 2007/0276292 | A1 * | 11/2007 | Hansma ............... A61B 5/4504 |
| | | | 600/587 |
| 2009/0171200 | A1 | 7/2009 | Sakai |
| 2011/0317898 | A1 * | 12/2011 | Shi ........................... G06T 7/30 |
| | | | 382/131 |
| 2012/0004594 | A1 | 1/2012 | Schulz et al. |
| 2012/0271215 | A1 | 10/2012 | Buckman et al. |
| 2012/0330091 | A1 | 12/2012 | Chisena et al. |
| 2013/0184627 | A1 | 7/2013 | Vedder et al. |

* cited by examiner

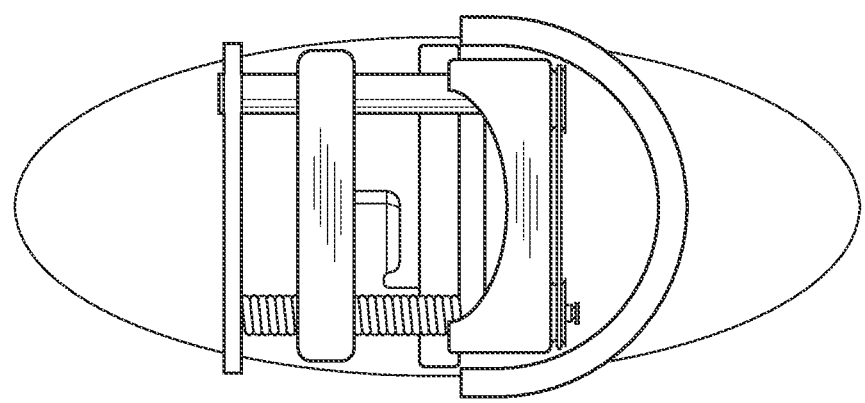
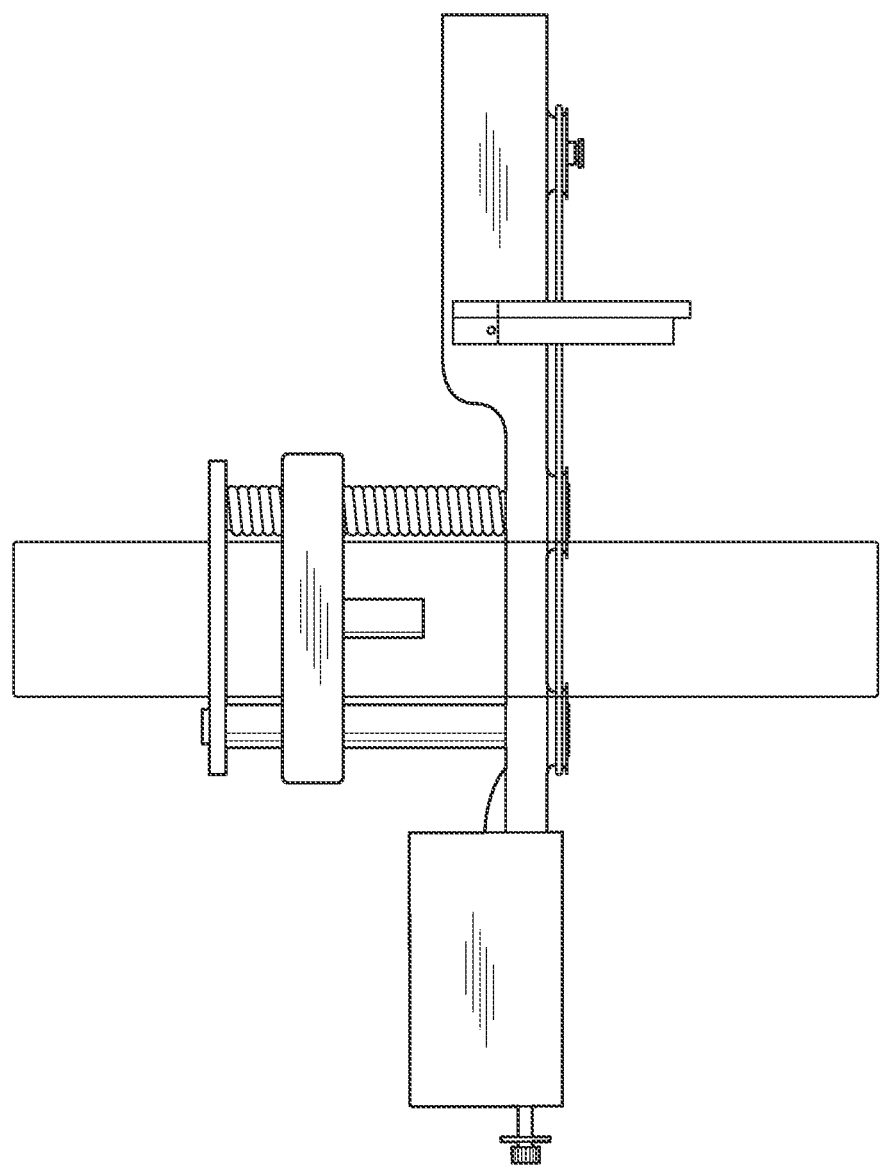
FIG. 9

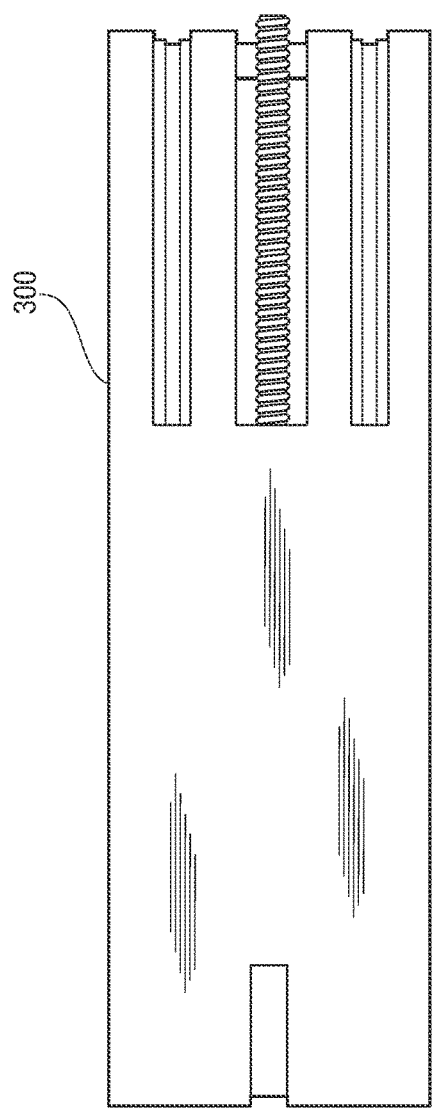
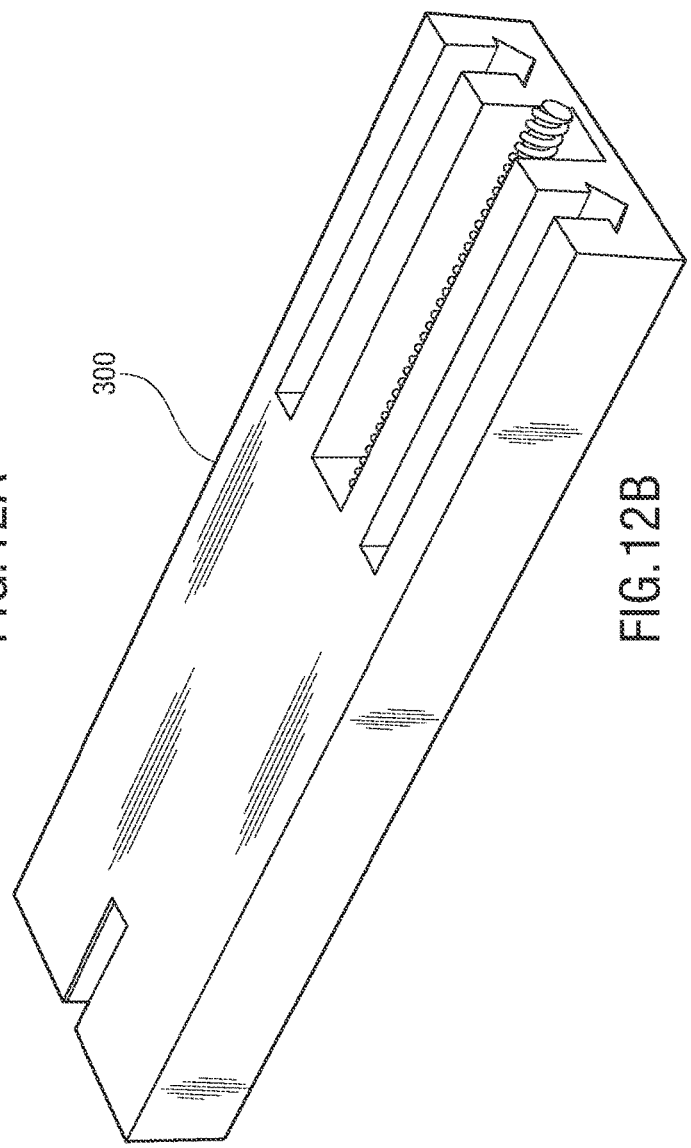
FIG. 12A
FIG. 12B

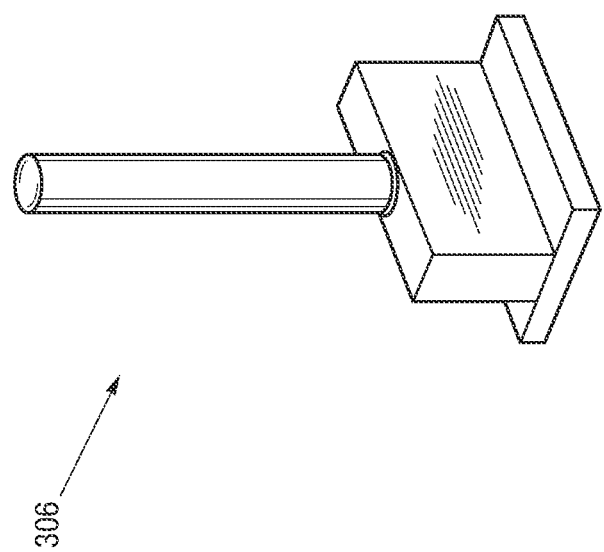

b. Displacements that occur in the base b. Displacements that occur in the pressure point

SYSTEMS AND METHODS FOR EARLY DETECTION OF FRACTURE HEALING

RELATED APPLICATIONS

The present application claims priority to and the benefit of U.S. Provisional Application No. 62/487,190, filed Apr. 19, 2017, which is incorporated herein by reference in its entirety.

FIELD

The present disclosure generally relates to imaging systems and methods for testing fractures and evaluating healing of fractures.

BACKGROUND

Bone fractures are common injuries. After skeletal injury, there is a highly regulated physiologic process which begins rapidly, and eventually culminates in repair of the broken bone. This physiologic response involves, among other events, an initial phase of inflammatory signalling which is followed by cellular migration, terminal differentiation, rapid cellular matrix deposition, neovascularization, mineralization of matrix, and after initial stabilization a long period of remodelling to mature healed bone.

A major healing defect that can occur during the healing of a fracture is non-union, which typically occurs with wide separation between bone ends and happens in one of two ways. Hypertrophic non-union results in the space between the bone ends being filled with cartilage and fibrous tissue. Meanwhile, atrophic non-union results in the bone ends being rounded and reabsorbed with no attempt at healing occurring. In unstable fractures, a bone fragment may also become displaced leading to incorrect or incomplete alignment during healing.

It can be important to detect healing defects earlier and to prevent premature cast removal in patients with fractures. Currently, clinicians and researchers have very limited means by which to measure and quantify this process. Quantifying the rate and extent of fracture repair would be useful for a number of reasons. Clinically, physicians would have a better sense of whether the process was progressing as expected, or whether some pertubation of the process was leading the patient to develop a delayed union or complete nonunion; identifying these complications earlier in the healing process might lead to more rapid intervention and hasten recovery. In addition to clinical benefit, measuring the rate and extent of bone healing would be crucial for researchers who are designing methods for accelerating this process, or addressing impaired fracture healing with pharmacologic treatment.

In the first instance, clinicians currently use plain radiographs to estimate the rate and extent of bone repair. Since first used to image bone in 1896, plain radiographs have changed little. Radiographs provide quite limited 2 dimensional information that is at best derivative. Static x-rays cannot, for example, measure how much load a fracture might be able to withstand, or whether small loads might further displace a fracture. Accordingly, physicians frequently immobilize or restrict a patient for arbitrary lengths of time; this is not because all wrist fractures require six weeks to heal, for example, but because the fidelity with which physicians can measure healing is too imprecise to allow for better clinical judgement.

Similarly, this lack of fidelity makes conducting clinical trials for pharmacologic agents which might accelerate or improve the healing process nearly impossible. While standard CT scans can provide a greater degree of precision and three dimensional resolution of fractured areas, the large amount of radiation involved in clinical CT scans makes their repeated use in clinical trials impractical.

A wide range of physiologic interventions have been tested in animals models going back to the mid 1970s, and a number of drugs which affect various stages of fracture repair have demonstrated positive effect on the healing skeleton. Yet currently, almost none of these medications have been tested in humans or have approval for use in accelerating fracture repair. This gap between bench research and clinical application largely exists because the fracture repair process itself takes a varying amount of time from person to person. Many factors can influence whether broken bones heal rapidly or slowly, or whether they develop delayed or non-union complications. These might include diseases such as diabetes or renal failure, medications such as corticosteroids or nonsteroidal anti-inflammatory medications, or patient related factors such as smoking or poor diet.

In a general sense, fractures are "healed" when they can bear physiologic loading without pain or displacement. However, clinicians cannot currently measure the extent to which a bone can bear load, or how much displacement actually occurs under a standard set of loading conditions. Instead, clinicians use "x-ray bridging" as a proxy for mechanical integrity, because no better measurement currently exists. Having a simple, reproducible, and low risk methodology for assessing mechanical integrity and displacement under load would give a better and more direct measurement of the true ability of the bone to bear load, rather than relying on a less precise and indirect methods.

In addition to improving clinical decision making, a reproducible method for quantifying physiologic loading capacity of bones which are healing in vivo would be a far more accurate means of assessing the effectiveness of pharmacologic interventions. Currently, large numbers of patients with complex fractures, such as open tibia fractures, are required to determine the effect of medications and devices on fracture repair. The low fidelity of x-rays to determine healing means that large numbers of patients have to be enrolled in studies which use fracture repair as an endpoint. As a result, clinical trials of fracture bones are only conducted infrequently; this is not because there are few targets for improving bone physiology, particularly in the diabetic or other at risk populations. Rather, it is the difficulty in assessing the extent to which candidate drugs are impacting physiologic healing which limits these trials. If the methodology for assessing repair were far more precise, then far fewer patients would need to be enrolled and studied to determine the effect of these agents on healing bone.

SUMMARY

The present disclosure generally relates to imaging systems and methods for testing and evaluating healing of fractures.

In some embodiments, there is provided a fracture testing system, comprising: an imaging device configured to image a bone fracture in a bone before and after the application of force thereto; a force application mechanism configured to apply a controlled force to the bone fracture such that the bone fracture displaces by a threshold amount; and proximal and distal supports configured to support the bone at locations proximal and distal of the bone fracture. In some embodiments, the force application mechanism includes an expandable member. In some embodiments, the expandable member is configured to inflate using a pneumatic system that can be adjusted manually or electronically such that the expandable member applies the force to the bone fracture. In some embodiments, the system further comprises a strain gauge or load cell to measure a strain on the bone. In some embodiments, the force application mechanism is configured to bend the bone to cause a displacement of the fracture. In some embodiments, the displacement is between about 82 microns and about 500 microns. In some embodiments, the displacement is between about 164 microns and about 250 microns. In some embodiments, the imaging device is High Resolution Peripheral Quantitative Computed Tomography (HR-pQCT).

In some embodiments, there is provided a fracture testing system, comprising: an imaging device configured to image a bone fracture in a bone before and after the application of force thereto; and a fracture testing device comprising: a base configured to receive an arm of a patient having the bone fracture; a force application platform, wherein the force application platform is moveable relative to the base along one or more guide rods; an inflatable force applicator disposed on a side of the force application platform facing the base, such that the force applicator can be positioned in contact with the arm of the patient; a pump in communication with the force applicator so that the pumping mechanism can inflate the force applicator to a desired pressure to apply a desired force on the fracture, wherein the fracture testing device is placed relative to the imaging device to enable the imaging device to image a displacement of the fracture. In some embodiments, the fracture testing system further comprises a strain gauge or load cell to measure a strain on the bone. In some embodiments, the force application mechanism is configured to bend the bone to cause a displacement of the fracture. In some embodiments, the displacement is between about 82 microns and about 500 microns. In some embodiments, the displacement is between about 164 microns and about 250 microns. The fracture testing system of claim 8 wherein the imaging device is High Resolution Peripheral Quantitative Computed Tomography (HR-pQCT).

In some embodiments, there is provide a method of analysing a bone fracture, comprising; stabilizing a bone having a fracture including a first support point located distal of the fracture and a second support point located proximal of the fracture; applying a force to an area of the bone having the fracture to cause a displacement of the fracture; imaging the bone during the application of force thereto; and comparing the image of the bone during the application of force to an image of the bone without the application of force to determine the state of the fracture. In some embodiments, the method further comprises comparing the images with and without the application of force allows for the measurement of bone strain of the fracture. In some embodiments, the measurement of bone strain is correlated to a particular stage of the healing process of the bone fracture. In some embodiments, the displacement is between about 82 microns and about 500 microns. In some embodiments, the displacement is between about 164 microns and about 250 microns. In some embodiments, the application of the force results in bending of the bone to cause the displacement of the fracture. In some embodiments, the method further includes measuring the displacement of the fracture.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 9 is a front and side view of an embodiment of a strain gauge;

FIG. 12A and FIG. 12B illustrate top and isometric views of the base and worm screw of the tensile loading design shown in FIG. 5;

FIG. 13 illustrates an isometric view of the hand peg of the tensile loading design shown in FIG. 5;

DETAILED DESCRIPTION

Figure 1:
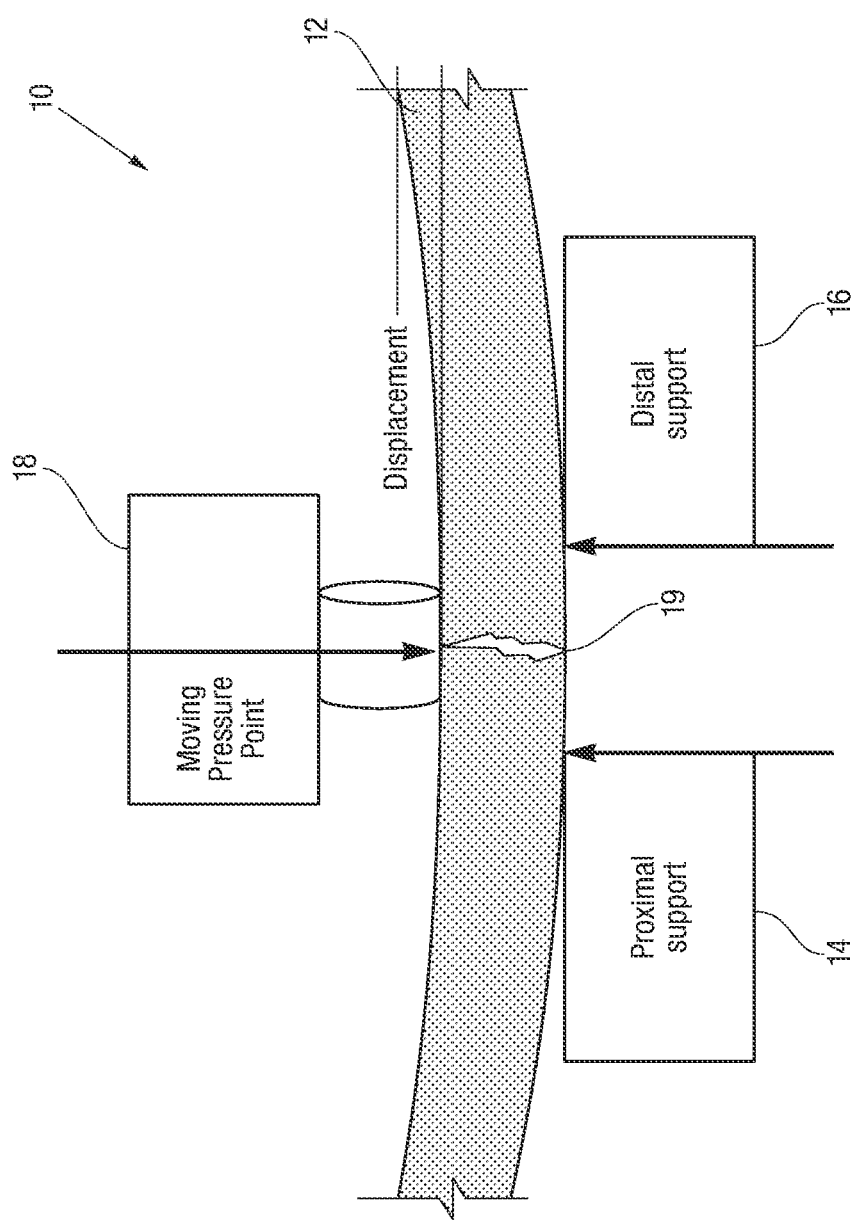
FIG. 1 illustrates a free body diagram of a wrist in 3-point bending.

In reference to FIG. 1, the instant disclosure provides methods and systems for evaluating a bone fracture. In some embodiments, a known mechanical load is applied to a fracture to produce a small displacement, which can be detected by an imaging modality. Bone strain can then be measured and correlated to a particular stage of the healing process such as, for example, through standard elastic displacement models commonly used in materials engineering applications. Bone strain can also enable the measurement of strength recovery in the fracture callus. By creating the measurement tool for bone strength recovery, the device can also aid in early detection of healing defects, and the testing and development of fracture healing therapies. In some embodiments, the device can allow doctors to know how much a bone has healed, if it is healing properly, when the bone has finished healing, and to decide on further treatment for the patient if necessary.

In some embodiments, there is provided a fracture-healing test device for use with a high resolution imaging method to allow physicians to measure bone healing in patients with various types of fractures, such as, for example, Colles' fractures. In some embodiments, a device can be used to quantitatively measure bone strength recovery in healing distal radius fractures. In some embodiments, the device can aid in improving patient outcomes by allowing physicians to assess bone healing stage, provide a framework for the design of similar devices for other common fracture sites, and create a device that can be used to assess the effectiveness of new interventional drugs and therapies.

For example, it can be difficult for doctors to see the extent of healing in fractures during the healing period. This can result in premature cast removal and healing complications such as failure to detect healing defects (including delayed or nonunion defects) early enough to most effectively treat them. In some embodiments, the instant methods and devices can be used to measure fracture healing rate. In some embodiments, such tests can be used to test impact of various therapies on fracture healing.

The device can be configured to apply a known mechanical load to healing distal radius fractures to produce a detectable strain in an imaging modality. This measurement can be correlated with the extent of healing to inform proper treatment and to evaluate healing processes. The instant systems and methods can allow physicians to evaluate the degree to which fracture healing has occurred, and to aid physicians in making accurate treatment decisions.

In some embodiments, a device, testing methods, and data analysis methods are provided that can allow for inference with the mechanical properties of a (bone) fracture callus non-invasively. This technology can also be used with various imaging techniques to follow a patient's fracture healing over time as a clinical tool.

A fracturing testing device can encompass a highly precise and reproducible system by which load can be applied in vivo to healing human fractures, and the resultant displacement can be assessed with three dimensional accuracy. By understanding the applied load parameters, and accurately measuring with high fidelity the displacement which occurs under this load, this system rapidly and reproducibly quantifies the mechanical environment of the healing fracture. This has important implications both for clinical medicine and for quantifying the effect of various pharmacologic interventions designed to accelerate and improve fracture repair.

In some embodiments, a device applies a non-damaging traction force on a broken limb while the limb is positioned inside an imaging modality, such as inside the bore of that can be used to track the positions of bones with high precision (for example, <0.25 mm resolution). The traction force can either be in axial compression tension, or in bending, and can be large enough to displace unhealed fracture fragments measurably, but not so large that the healing callus would be damaged or that any soft-tissue surrounding the area is painful or injured. The device can apply a load to a fractured bone in order to quantify the strength of the distal radius during healing. In some embodiments, the device applies a load and calculates the current elastic modulus of the bone and compares it to the normal projected elastic modulus of a bone at the same time of healing. An image with the applied load can be used to show the displacement of the bone and calculate the elastic modulus, and a doctor can then decide if the fracture is healing properly, or if it has early signs of a healing defect by comparing the actual modulus of the bone to the calculated modulus.

In some embodiment, the device can have various features, including, but not limited, to radiolucence, compactness, repeatability, force capability to displace a healing fracture (for example, 162 microns to 2 mm), and the ability to apply a force small enough to prevent injury or pain to the patient. For example, as a bone is slowly separated, once it reaches 2 mm of displacement the soft tissue begins to undergo damage which slows the healing process. In some embodiments, the applied force can be on the lower end in order to get a small displacement, but still large enough to pass the minimum threshold for an imaging device, such 164 microns for a CT machine. For example, the minimum displacement detectable on a CT machine is 82 microns. However, in order to get an accurate enough reading to produce the desired results, 164 microns is the minimum displacement detectable on a CT. In some embodiments, the targeted displacement can be 250 microns, which is ⅛ of the maximum displacement a bone can undergo before the healing process is compromised.

In some embodiments, the targeted displacement can be between about 82 microns and about 500 microns. In some embodiments, the targeted displacement can be between about 164 microns and about 500 microns. In some embodiments, the targeted displacement can be between about 200 microns and about 500 microns. In some embodiments, the targeted displacement can be between about 82 microns and about 250 microns. In some embodiments, the targeted displacement can be between about 164 microns and about 250 microns. In some embodiments, the targeted displacement can be between about 200 microns and about 250 microns. In some embodiments, the targeted displacement can be between about 82 microns and about 1000 microns. In some embodiments, the targeted displacement can be between about 164 microns and about 1000 microns. In some embodiments, the targeted displacement can be between about 200 microns and about 1000 microns.

Figure 2:
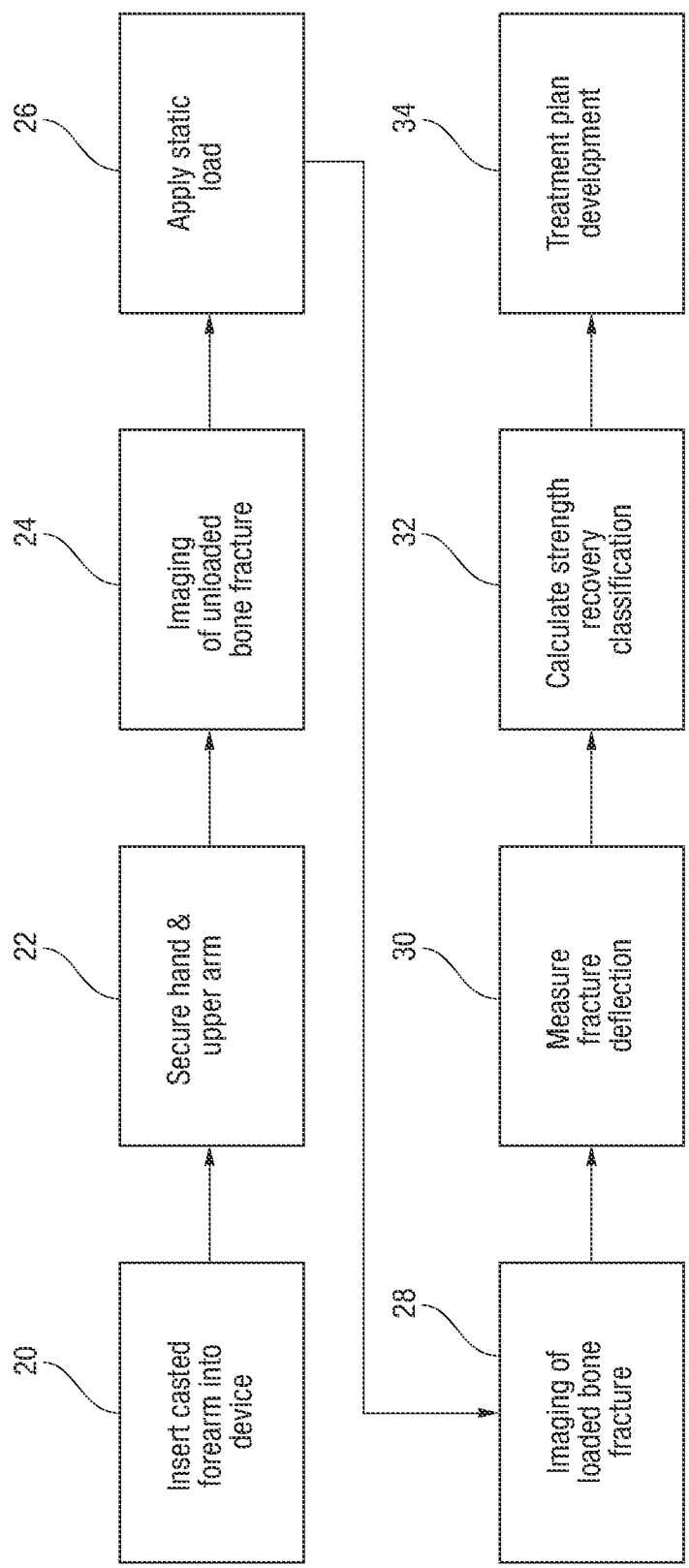
FIG. 2 illustrates an embodiment of a product function flowchart of an method for detecting fracture healing.

FIG. 2 shows flowchart of the steps for an exemplary system for the analysis of fracture healing, using a forearm fracture as an example. It will be understood that the device can be used for any limb or bone type. A bone to be analysed, such as a forearm, is inserted into a device (step 20), and the bone and portions of the body proximal and distal to the bone are secured (step 22), such as a hand and upper arm. For example, a hand and elbow gripping mechanism can be used to keep the patient's arm secure. An image is taken of the unloaded bone fracture (step 24). After this image is taken, a static load is applied to the bone (step 26), and an image is taken of the loaded bone fracture (step 28), and the amount of force that is applied to the fracture can be measured. The amount of fracture deflection can be measured (step 30), and a strength recovery classification can be calculated (step 32). For example, from the image, the stage of recovery that the fracture is in can be determined by performing stress analysis calculations. Using this information, a treatment plan can be developed (step 34).

Device

A fracture testing device 10 can utilize a three-point bending method for testing a fracture in a bone 12, as shown in FIG. 1. In some embodiments, a bone 12, such as a forearm, is secured and can serve as the two support points (a proximal support 14 and distal support 16) for the three-point bending method. A force application mechanism 18 can be used to apply a downward force onto the bone, as the third point to apply the bending loading as shown in FIG. 1. This force that is applied to an area of the bone having a fracture 19 can be used to determine the level of healing of the fracture.

The device could be configured several ways. For the application of axial tension, in some embodiments, a device can grip the limb of interest using a combination of straps, cuffs, and other positioning devices to comfortably restrain the limb. The positioning devices can each be fixed to anchoring mounts. The limb can be gripped at the distal end (towards the tip of the limb) and proximal end spanning the fracture site. Compression or tension can be applied by moving the two anchoring mounts towards or away from each other. The force can be regulated in a variety of ways, for example by specifying a fixed displacement or specifying a fixed force that is applied. Force can be measured with instrumentation such as a strain gauge or load cell, and can be adjusted manually to achieve a specific target. In some embodiments, the device can include a non-back-drivable screw system combined with pulleys to regulate force and displacement application. In some embodiments, the device can include an expandable member, such as an inflatable balloon, with a pneumatic or hydraulic system that can be adjusted manually or electronically.

For application of bending moments, the limb can be similarly fixed, but positioning devices can be oriented such that they could both pull downward on a horizontally-oriented limb. Between the two positioning devices, a raised area would serve as a fulcrum about which the bending would occur. Bending moment would be regulated by either specifying a fixed displacement of the anchoring mounts, or by specifying the force with which the limb is pulled downward on either side of the fulcrum. The tensile force can be measured through a load cell or strain gauge, for example, and be manually controlled with a screw-driven system. In some embodiments, the device can apply a force to twist the fragments of the bone spanning the fracture.

The general concept is that the fracture site is imaged with no traction force applied, and again with a known traction force applied. The displacement of the fragments or ends of a fracture can be measured by comparing the two images. Given that the traction force is also known, an estimate of the fracture callus stiffness can be obtained.

The method can involve identifying the bone fragments on each of the images (with, and without traction) along with measuring fracture callus mineralized tissue volume. By applying traction and subtracting out the other passive soft tissue structures' stiffness, an estimate of the fracture callus stiffness can be calculated. The passive soft tissues, including muscle, tendon, and skin surrounding the fracture site, have negligible stiffness compared to bone. This is more of a consideration in the tension-based model. The contralateral (uninjured) hand can be used to determine the passive force/displacement of the soft tissue only, and then the value would be assumed to be similar on the injured side. This is an early indicator of whether the fracture is healing at a normal rate, or whether there is a delay in healing. Calculations for beam-bending can be used. In some embodiments in the bending version of the device, the bone can be loaded in 3-point bending. Thus, the displacement of the fragment at the palmar (bottom) surface of the bone is going to be maximal right under the force application point. In one example, to obtain some basic estimates, it can be assumed that the radius is a cylinder with outer diameter of 2.5 cm and inner diameter of 2.0 cm. A healing fracture can have a modulus similar to soft tissue (<0.1 MPa) when it is fresh, around 5-10 MPa when it is in a soft-callus stage, and 5-10 GPa in hard callus stage. Using this, it can be estimated that to create fragment displacements ranging from 164 micron to 2 mm (corresponding to the minimum detectable and maximum allowable) a fresh fracture would require less than 1 N force (for example, 0.1 to 1), an early stage 9-48 N, mid-stage 30-150 N, and intermediate somewhere from 68-400 N. The concept is that a normal can be benchmarked, and then something that is not normal can be identified as the stiffness being below some value at some given time point.

In some embodiments, a fracture testing device of the present disclosure is used inside an imaging device. A bone, such as an elbow, is stabilized, and a portion of the body proximal to the bone is grabbed to apply a traction force. Displacement can be measured using a plurality of images using the equation stiffness=force/displacement. As long as fragment motion is less than a threshold, such as, for example, about 2 mm to 3 mm, healing is not disrupted. Non-union and delayed union are common clinical complications, and using these techniques these complications can be found for earlier intervention to promote fracture healing. A major healing defect that can occur during the healing of a fracture is non-union, which typically occurs with wide separation between bone ends and happens in one of two ways. Hypertrophic non-union results in the space between the bone ends being filled with cartilage and fibrous tissue. Meanwhile, atrophic non-union results in the bone ends being rounded and reabsorbed with no attempt at healing occurring. In unstable fractures, a bone fragment may also become displaced leading to incorrect or incomplete alignment during healing. Interventions (pharmaceutical, or the use of electromagnetic stimulators to promote bone healing, for example) exist and this type of imaging can help these technologies to be applied where they are most needed, in a timely manner before long-term problems occur.

Imaging Techniques

There are several methods for the medical imaging and evaluation of the structural integrity of bones. Suitable imaging modalities include, but are not limited to, X-ray radiographs, MRI, CT, High Resolution Peripheral Quantitative Computed Tomography (HR-pQCT), and sonographic methods. The imaging techniques presented here may differ by their mode of acquisition and sensitivity to tissue properties.

In some embodiments, mechanical loading can be applied to produce a displacement of the healing bone that is measurable using an imaging technique. This permits the calculation of elastic modulus of the bone callus, a measure of stiffness and strength recovery in a healing bone. For example, distal radius fractures occur primarily in post-menopausal women, for whom the healing period and rate is not readily predictable in an individual. This leads to failure of early detection of healing complications such as delayed union or nonunion, conditions which may lead to excessive casting times, and require monitoring or intervention for optimal patient outcomes. Clinically, the ability to measure stiffness in a healing fracture provides valuable information to healthcare providers.

For example, the device can be designed for use with HR-pQCT imaging, which has a voxel (3D pixel) resolution of 82 micrometers. This means that the minimum measurable displacement would traverse two voxels, a distance of 164 micrometers. In some embodiments, the targeted displacement can be between about 82 microns and about 500 microns. In some embodiments, the targeted displacement can be between about 164 microns and about 500 microns. In some embodiments, the targeted displacement can be between about 200 microns and about 500 microns. In some embodiments, the targeted displacement can be between about 82 microns and about 250 microns. In some embodiments, the targeted displacement can be between about 164 microns and about 250 microns. In some embodiments, the targeted displacement can be between about 200 microns and about 250 microns. In some embodiments, the targeted displacement can be between about 82 microns and about 1000 microns. In some embodiments, the targeted displacement can be between about 164 microns and about 1000 microns. In some embodiments, the targeted displacement can be between about 200 microns and about 1000 microns.

A semi-automatic process called 'contouring' is applied to separate the bony tissue from the surrounding soft tissue based on the grayscale value of the images. In this application, displacement can be measured by voxel position of the edge of the bone in the direction of loading in the field of view in the unloaded vs. the loaded state. Knowing the force applied and the bone's cross sectional geometry, the elastic modulus of the bone can be computed using standard stress models and used as a clinical measure of healing extent.

In some embodiments, a radiolucent in-scanner device can be designed and fabricated that applies a known mechanical load to a fractured radius to observe bone displacement and measures the strength of healing distal radius fractures in various types of imaging, for example High Resolution peripheral Quantitative Computed Tomography (HR-pQCT) imaging. By measuring the strength and bone displacement, the device can help prevent premature cast removal and allow for early identification of healing complications.

In some embodiments, guiding objectives for the device can include, without limitation: 1. The device can produce a displacement visible in an HR-pQCT image (~165 microns minimum) or another imaging modality: A displacement that is visible in the scanner begins at a size of 82 microns, the voxel (cubic pixel) resolution of the scanner. Displacement can most reliably be seen when it spans two or more voxels, about 165 microns. In some embodiments, the device will achieve highly visible displacements of 1-2 mm. 2. Permit the testing of callus strength in a healing fracture, such as a distal radius fracture. The device can apply a mechanical load to test the recovery of strength in fracture calluses on the distal radius. This mechanical load can correlate with degree of fracture healing (for example, the greater the applied load, the more the fracture has healed). 3. Position and restrain the patient to ensure image quality: It is important to ensure patient comfort, to secure the hand and forearm to limit movement during the scan, and to reduce the risk of motion artifact in the HR-pQCT images.

The device can be configured to apply a sufficient force to produce a detectable displacement of the bone at the fracture site; however, the force cannot cause damage or disrupt healing in the fracture callus throughout the full healing process. The device can be configured to produce both small and larger forces, depending on the degree of healing. For example, it is believed that a maximum displacement of 1-2 mm is non-damaging and can be beneficial to bone callus formation. In some embodiment, the device can be configured to be sufficiently rigid to restrain and apply the needed forces to the patient without itself displacing to ensure measurement quality and repeatability.

There are several physical design requirements of the device to consider. As mentioned above, the device can be configured to apply a non-damaging force and displacement, apply a repeatable and a tolerable level of force, have appropriate dimensions, be radiolucent, and be sufficiently rigid to ensure measurement quality. Additionally, the device can be right and left arm compatible, fit an average post-menopausal woman, be ergonomically friendly, easily manufacturable and cleanable, and cost-effective. It will be understood that the device can be configured to include any combination of these features.

In some embodiments, the device can be configured to apply a non-damaging force and displacement. This can be important because a broken bone that is in early union typically has a Young's modulus (or stiffness coefficient) of 5-10 MPa, while a fully healed bone has a Young's modulus of 15-20 GPa. For example, a lower amount of force can cause a damaging displacement to a bone that has partially healed compared to a fully healed bone. Furthermore, it is believed that a displacement of 1 mm is actually beneficial to bone callus formation through a process called distraction osteogenesis. A maximum distraction of 2 mm begins to slow the bone healing process if the distraction is performed repeatedly throughout the healing process. Meanwhile, a callus distraction greater than 2 mm can begin to damage the healing fracture. Calculations can be done to determine the amount of force required to displace soft tissue and bone during different stages of healing. The device can be configured to apply a repeatable force and displacement to patients independent of varying muscle and bone geometries.

In addition to applying a non-damaging and sufficient force, the device can be configured to produce a tolerable amount of pain or discomfort, which corresponds to no more than a 4 or 5 on the standard medical Self-Rated Pain Assessment Scale of 1-10. The use of the device does not produce a degree of discomfort or pain that is intolerable to most patients.

An additional need is that the device be sized and shaped to fit within an imaging modality. For example, a CT scanner has dimensions of 7.5"×31"×5.5". The key constraints include the height, which cannot exceed 7.5" and the width, which cannot exceed 5.5". The device can extend somewhat beyond the scanner in length. In some embodiments, the device is sized and shaped to fit inside the imaging device, for example a HR-pQCT scanner imaging area. For example, dimensions of an exemplary HR-pQCT scanner imaging area are 5.5" wide by 7.5" tall by 31" deep. Furthermore, the device can be radiolucent, which means transparent to X-rays. The device can be configured to be radiolucent within the imaging zone so as to provide a minimum image artifact in an image, such as the HR-pQCT scan image. Materials that are radiolucent include but are not limited to plastics and several types of metals, such as aluminum, stainless steel, and titanium. In some embodiments, plastic materials can be incorporated into the design because they are more radiolucent in comparison to metals. Another design consideration is that the device fully restrains the imaged portion of the arm, so that there is sufficient image clarity and repeatability.

In some embodiments, the device can also be right and left compatible, such that the device can test distal radius fracture healing for both the left and right arms. In some embodiments, the device solution can be right/left compatible or can include modules for both sides. In some embodiments, the device can be sized and shaped to fit a variety of users. For example, the device can be designed to fit the average postmenopausal woman (this patient population represents over 70% of Colles' fractures). For example, when being used with an arm fracture, the device can also be sized and shaped to accommodate a range of wrist sizes. For example, the typical wrist size is ~6.5-7.5 inches in diameter for postmenopausal women who are the patient cohort that is most affected by distal radius fractures. The device can also be configured to be comfortable to patients and can be cleanable via standard medical procedures.

The device can also be configured to be easily manufacturable via standard manufacturing techniques, such as 3D printing, machining, or injection molding. Injection molding combined with carbon fiber mats can provide the flexural moduli needed to prevent device deflection. For example, the device can be formed using 3D printing with a Markforged Mark Two with carbon fiber and ONYX, a carbon fiber reinforced nylon filament. This technique allows for a high flexural moduli for 3D printed materials and fast production times as it is available in one of our advisor's labs. Carbon Fiber Reinforced PLA to 3D print the device can also be used, which also offers a high flexural modulus. In addition, standard ergonomic principles can be implemented in the device to assure patient comfort and device performance. In some embodiments, the device can be configured to be cleaned using standard medical cleaning procedures.

It will be understood that the device can be used for various types of fractures that occur in any bone or location of the body. For example, the device can be used with any of the long bones of the body, including but not limited to Colles' fractures and Smith fractures, which account for 10% of wrist fractures. In some embodiments, the device can be utilized while the patient is still wearing his/her cast. Additionally, the device can be able to distinguish between partial and complete fracture healing strength. It can also be useful if the device can be utilized in any patient population (i.e. children, adolescents, and men with distal radius fractures). In addition to wrist fractures, the technique can be applied to any anatomic location, such as, by way of a non-limiting example the ankle, distal tibia/fibula, proximal tibia/fibula, distal femur, proximal radius/ulna, and distal humerus. The device may be modified for specific anatomical geometry, and subjected to a loading regimen to measure stiffness of the healing callus. The device can be placed in the gantry of an imaging modality with adequate resolution to resolve minute changes in displacement resultant from the loading regimen, which may depend on the local anatomy and bone size to deliver the requisite force.

Force Application

Various methods of applying a force can be utilized. In some embodiments, a tensile load can be applied, and in some embodiments, a bending force can be applied. In both methods, the device restrains the hand and forearm during the scan to provide stability and ensure a clear image.

A strain gauge can be used to measure the force that is applied to the fracture, such as a distal radius fracture. Through the drive rods to the distal radius to two decimal places and this metric can be read electronically to the technician. Once the force is measured, an image of the distal radius under the mechanical load can be generated.

In some embodiments, a fracture testing device can include an inflatable component to apply force to bone. By inserting a balloon pump, a user can efficiently and safely apply a load to the patient's bone, for example an arm bone.

Various techniques can be used to apply force to bone. In some embodiments, pneumatic and hydraulic force applicators can be used. Pneumatic and hydraulic systems use compression properties to create a force, thus performing an action. Pneumatic systems compress gas, while hydraulic systems use the non-compressive properties of liquid in order to move a joint. Pneumatic systems tend to be slower but more accurate due to the need to build up pressure by compressing gas. Hydraulic systems are immediate and more powerful due to liquid immediately forcing a joint to move and therefore are used more in heavy machinery. In some embodiments, the pneumatic chamber is configured to apply pressure, and a pressure transducer is used to measure force, with a calibrated force/pressure relationship.

Figure 3:
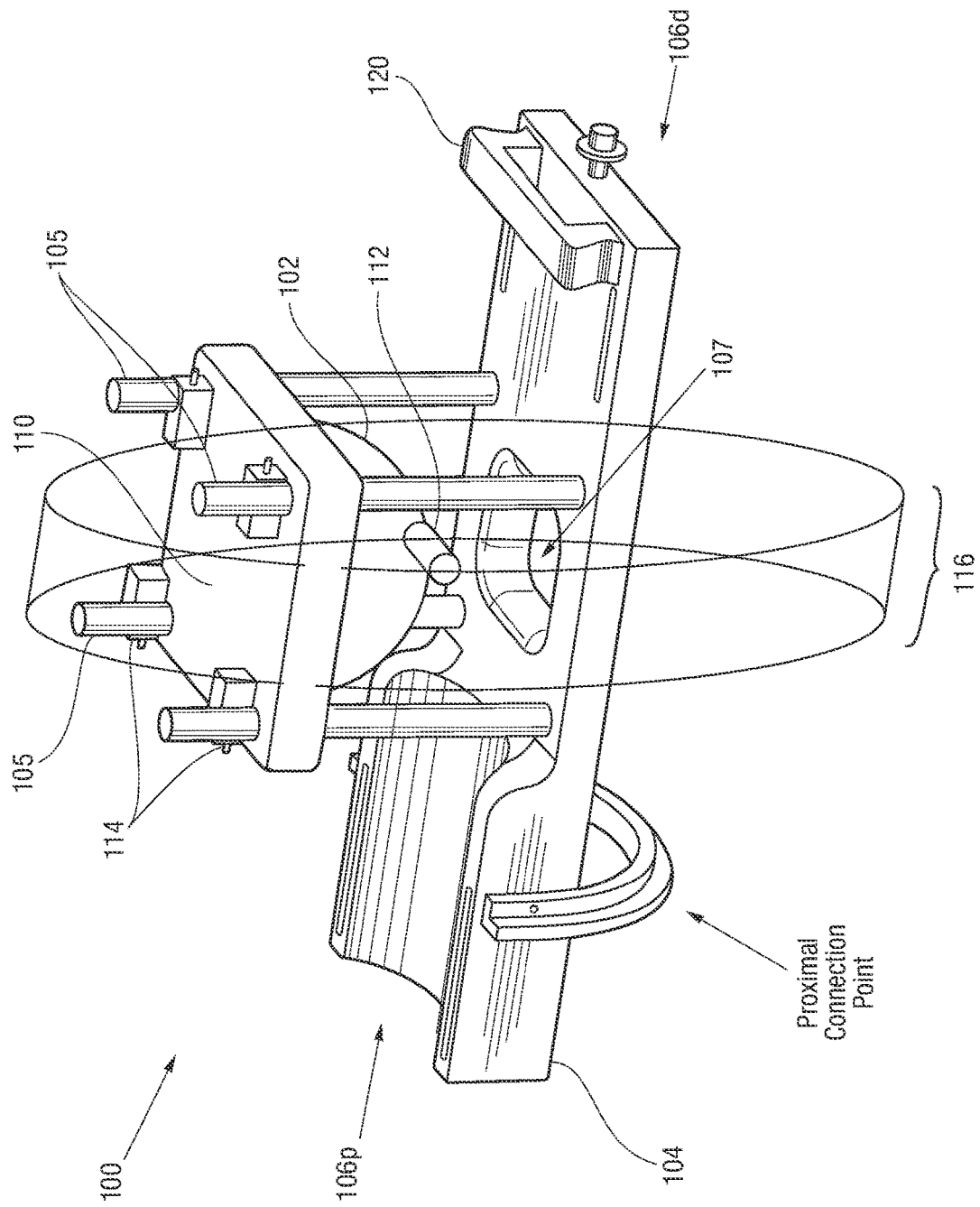
FIG. 3 illustrates an embodiment of a fracture testing device using an expandable member to apply a force to a fracture bone.

FIG. 3 illustrates an embodiment of a fracture testing device 100 including an expandable member, such as a balloon 102, for applying force to a fracture. The size and shape of the device 100 can vary, but in some embodiments a base 104 can include a plurality of guide rods 105. For example, in the illustrated embodiment the base includes four 0.5 in diameter dowels fixed and protruding upwards 7 in as the guide rods 105. The device 100 can include a small rod at a distal end 106d for the patient to grab a hold to and also curves along the side to rest their thumbs. The device 100 can also include two slits on both the distal and proximal ends 106d, 106p where two cinch straps can slide into to strap the patient's arm in to minimize movement within an imaging device. At the distal end 106d of the device 100 is a screw in order to quickly lock the device into place in the imaging device and also a lip on the proximal end 106p to allow the device 100 to rest at the edge of the imaging device to keep it in place. Once the patient places a portion of their body, such as their hand, on the base 104 of the device 100, a force application mechanism 110 is moved downward towards the patients until it gently rests on the patient's body that is placed in the base 104, such as the patient's wrist. In some embodiments, the force application mechanism includes a deflated balloon 102 and a large Delrin dowel 112 attached such that the force application mechanism can be slid down the four dowels with the dowel 112 being placed right at the fracture site of the patient. The force application mechanism 110 can be locked into place to prevent movement by using one or more tripod clamps 114 that slide onto the dowels until they reach the force application mechanism 110 where they are then screwed into place. The wrist is then loaded by an air pumping system that slowly inflates the balloon 102 which pushes the dowel 112 onto the fracture site, displacing the bone a small amount. A cutout 107 positioned substantially in the middle of the base 104 allows for the bone fracture to be unsupported so that it can properly be loaded in 3-point bending to produce the necessary displacement of the bone ends.

The base 104 includes a location for a bone, such as an arm, to rest. In some embodiments, the base 104 is flat towards a distal end 106d where the hand is positioned, but as it gets closer to a proximal end 106p where the forearm is placed the base 104 can curve upwards to provide comfort for the patient's arm. This forearm support can also be covered in padding to keep for patient comfortable. Also included on the base 104 is a clip on the distal end of the device in order to clip into an imaging device. On the proximal end is a lip which allows the device to lock into the scanner to keep in place. In the middle of the base 104 is an imaging region 116. This aids the doctor to have an idea of where the bone should be since this is the area where the imaging will take place. This hole also provides contact points in order to apply a three point bend to a portion of the bone, such as the wrist. The base 104 also has slits on both ends where cinch straps slide through to lock the patient's arm into place.

A finger support 120 is located at the distal end 106d of the base 104, and in some embodiments is in the form of a small rod that helps restrict patient's fingers from hanging off of the device. This keeps the procedure as repeatable as possible while also providing the patient with something to grip onto during the imaging procedure.

One or more guide rods 105, such as the four 12 mm inch plastic rods that are fixed into the base and protrude upwards 7 inches, can be included. These rods are used to guide the force application system down onto the patient's arm. This creates a much larger radiolucent region which means more of the patient's wrist can be seen without obstruction.

The force application mechanism 110 is included to apply a force to the bone fracture. In some embodiments, the force application mechanism 110 includes an inflatable force applicator, such as a balloon, and a dowel. The force applicator is the structure that holds the force application mechanism 110 together. It can include the balloon 102 and the dowel 112 attached thereto. The applicator keeps the balloon 102 and the dowel 112 from being pushed upwards as the load is being applied. By pumping up the balloon 102, the applicator stays put so the balloon begins to push the dowel into the fracture site of the patient's wrist, causing a three point bend. The dowel 112 is the piece that applies the force onto the fracture site. For example, the dowel can be in the form of a 12.5 mm Delrin dowel that is wrapped in neoprene for extra comfort. The dowel also has aluminum tape around it in order to see it in an imaging device, such as a CT scanner, to aid the doctor in aligning the dowel with the fracture site. In some embodiments, the dowel 112 can be attached to the balloon 104 with a rubber casing that was made with silicone in order to attach the dowel to the balloon while also being flexible enough to bend as the balloon changes shape during inflation. It has been found that there is a linear relationship between pressure in the balloon and the amount of force that is applied on the fracture. As such, the inflatable force applicator can be consistent and accurate, and can be inflated to a desired pressure to correspond to a desired force.

One or more clamps 114, such as two quick release tripod clamps, can be used to hold the force application mechanism 110 in place. The clamps slide onto the guide rods and once in place screw on to tighten onto the guide rods such that, when the balloon 102 is inflated, the force application mechanism is immobile.

Figure 4:
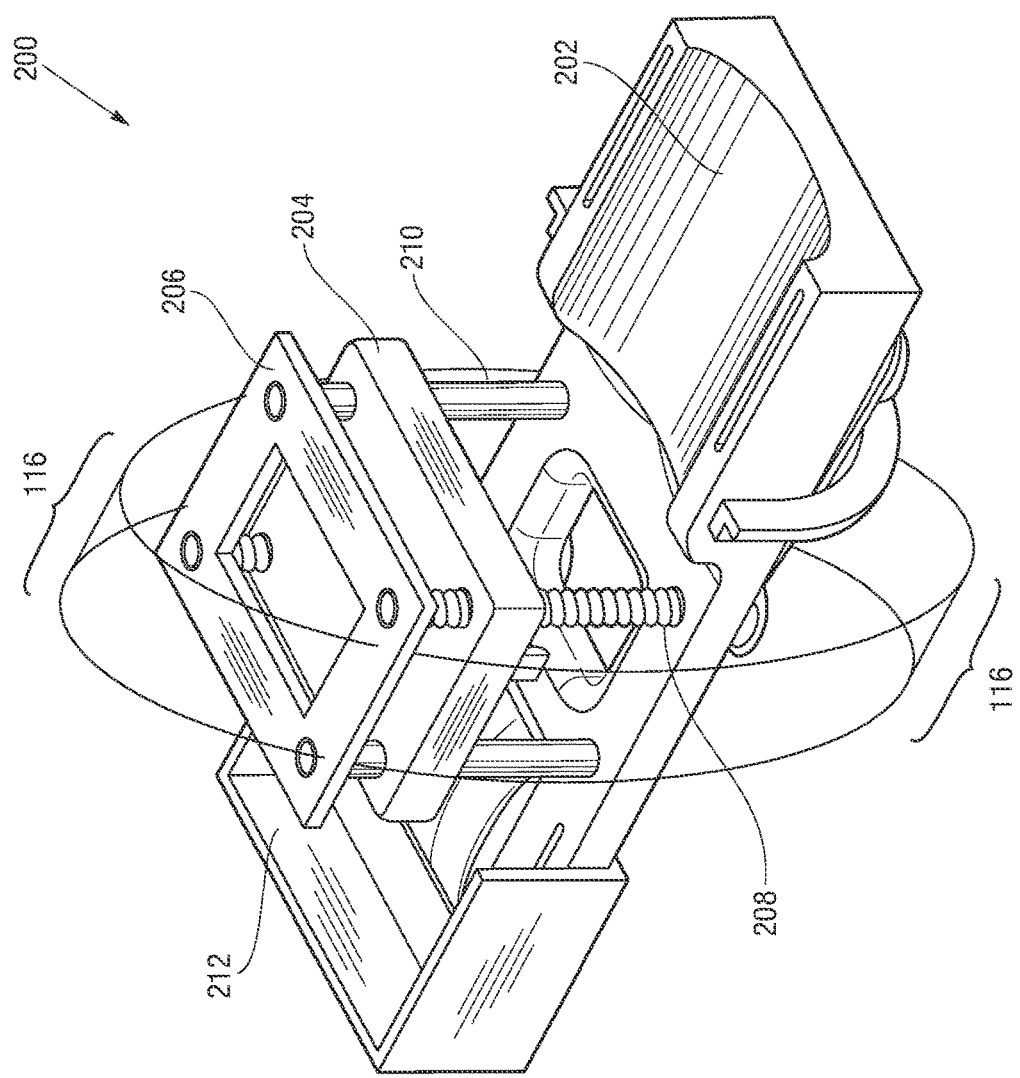
FIG. 4 is an isometric view of an embodiment of the device.

FIGS. 4-9 illustrate another embodiment of a fracture testing device 200. In some embodiments, a bone can be loaded in a three-point bending model. The device can include a base for the arm to rest upon, and a piece driven by a screw drive mechanism to apply a force to the top of the wrist. FIG. 4 shows an isometric view of the device.

Figure 5:
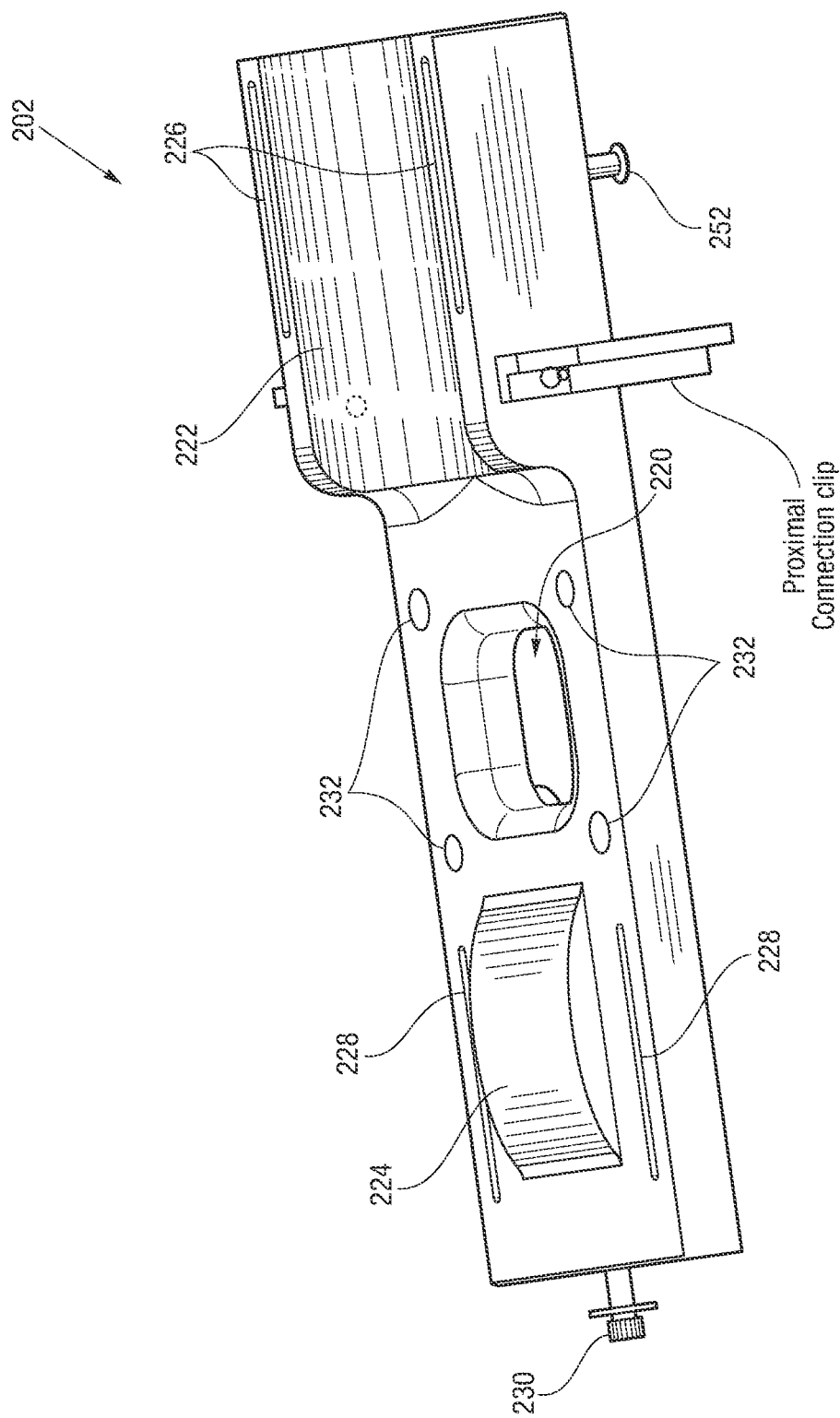
FIG. 5 is an isometric view of the base as a subassembly with associated parts.

The device 200 includes a base 202 that is configured to provide a rigid, comfortable support for the arm, as shown in FIG. 5. A cutout 220 positioned substantially in the middle of the base 202 allows for the bone fracture to be unsupported so that it can properly be loaded in 3-point bending to produce the necessary displacement of the bone ends. The base 202 includes an imaging section, a proximal support 222 such as a forearm rest, and a distal support 224 such as a hand rest. The forearm and hand rests can be padded with a medium density closed-cell foam which is curved to fit the natural curves of the arm and hand. The arm support can be fitted with different thicknesses of padding from the standard SCANCO forearm cast to allow for it to be adjustable for varied arm sizes. The forearm and arm supports contain slots 226, 228 on the side, and velcro straps can be fed through the slots to help keep the patient still and secure during the scan using the imaging device. On the distal end of the device is a distal connection clip 230 including a screw and a washer which connects into the end of the imaging device. The proximal end contains a ring which sits on the two screws near the outside port of the machine.

Figure 6:
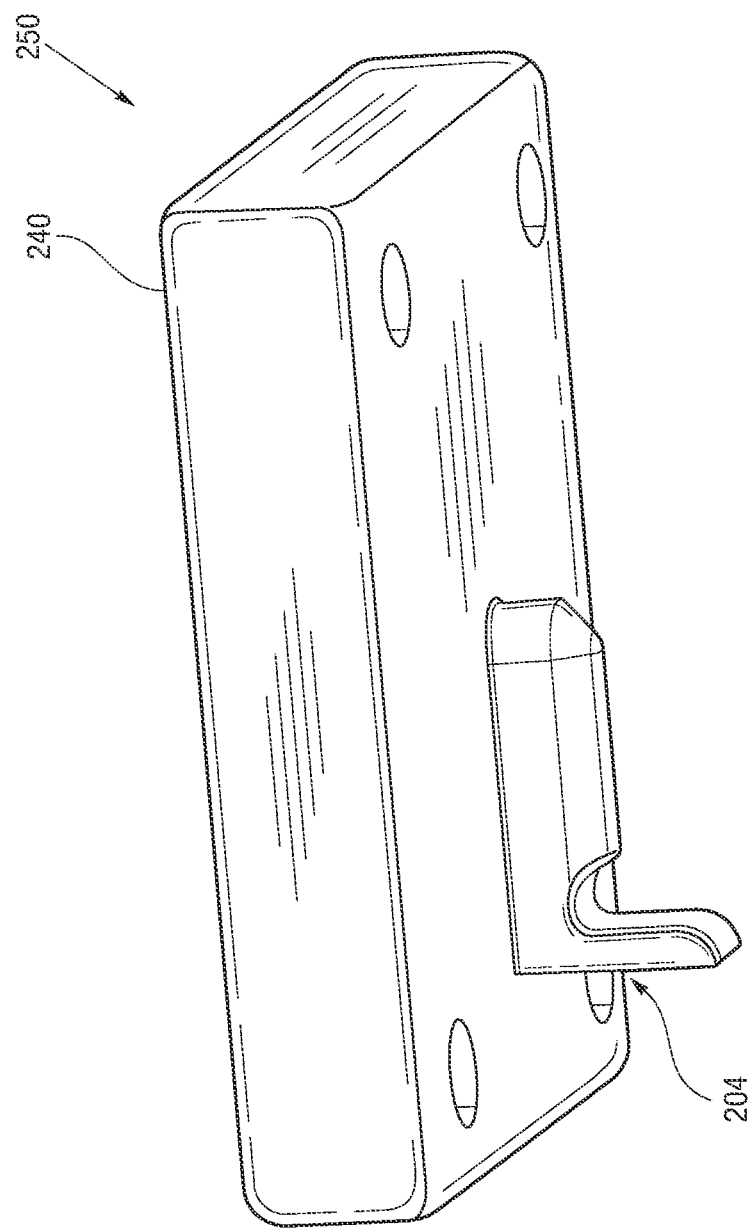
FIG. 6 is a diagram of the pressure point piece.

A pressure point 204 can include a lightly padded protruding surface, which applies the force to bone, such as the wrist. The side of the piece contains a longer protrusion to line up with the styloid process on the side of the distal radius to allow for the arm to be properly lined up under the pressure point 204 in a repeatable fashion. The pressure point 204 is attached to a rectangular support, which contains threaded holes to allow for the movement up and down based on the turning of the screws. The support 240 is shown in FIG. 6.

A top piece 206 can be in the form of a thin frame such that the plurality of rods 210 are fixed therein so that the drive rods 210 remain straight and drive properly without buckling inwards. The drive rods 210 are positioned within guide rod holes 232 in the base 202.

A screw drive 208 can be in the form of two steel ½-40 inch threaded rods, 5.5 inches in length, that are used to drive the device. The threaded rods are fixed diagonally around the cutout into the base, but allow for rotation. The rods are to be threaded in the middle portion only where the pressure point piece can be driven up and down. The rods are retained using threaded nuts on the bottom of the device. Because the rods are made out of standard metal materials, they are placed outside of the imaging region. This way, they could be readily available for purchase and would not require custom machining. In the case that localized stresses around the rods are excessive for the plastic, metallic inserts can be placed to bear the load. A rod with 40 threads per inch was chosen because testing showed that 13 threads per inch did not allow for enough fine force adjustment as maximum force was reached before a 180 degree turn of the rods. 40 threads per inch was the highest thread count commercially available. The rods are fixed, allowing for rotation into both the base and top support pieces. The pressure point piece is threaded onto the rod so that when the rod is turned the piece is driven downward to apply the force.

Guide rods 210 can be in the form of ½ in diameter non-threaded rods made of delrin and are 5.5 inches in length. They are fixed into the top and base pieces. The pressure point piece moves in the z direction along them.

A hand guard 212 can be configured to slide on around the end of the part to protect the hand in the case of any contact with the inside of the scanner.

Figure 7:
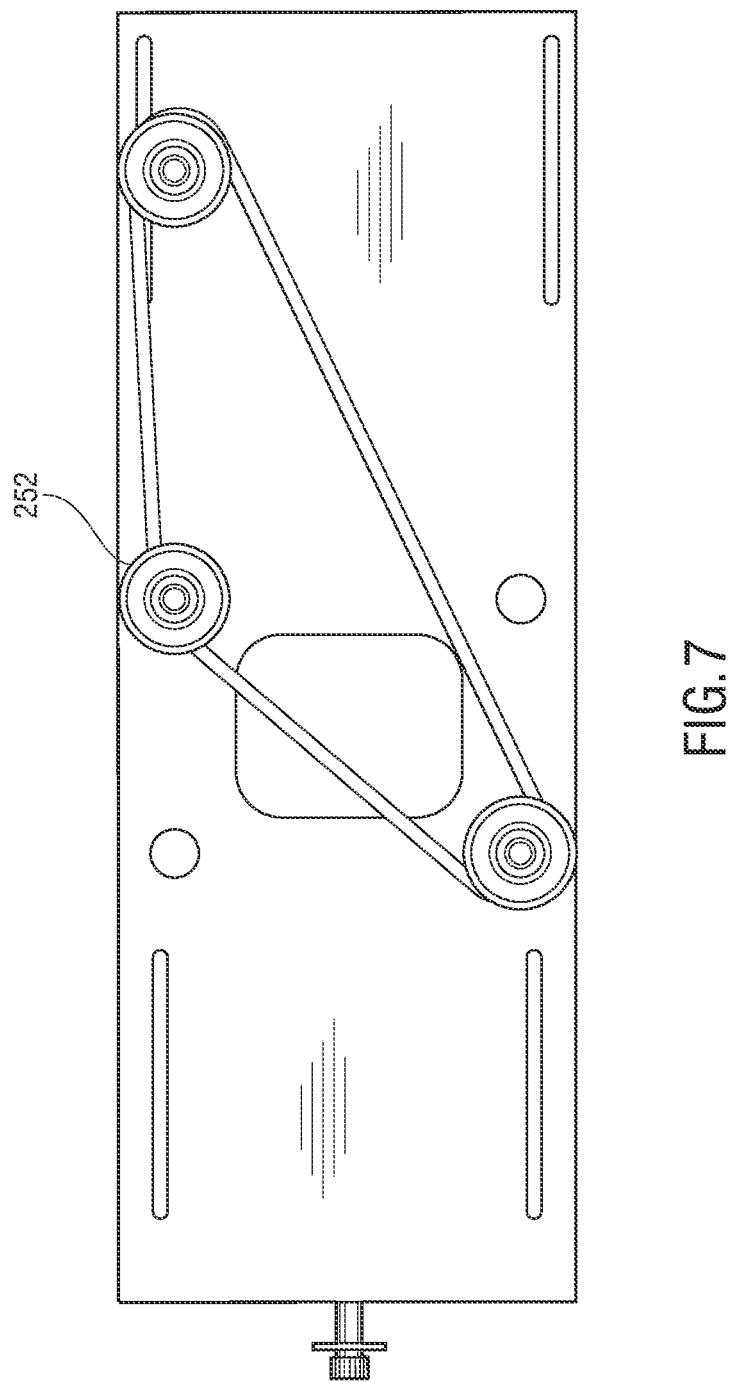
FIG. 7 is a bottom view of a base piece detailing pulley system.
Figure 8:
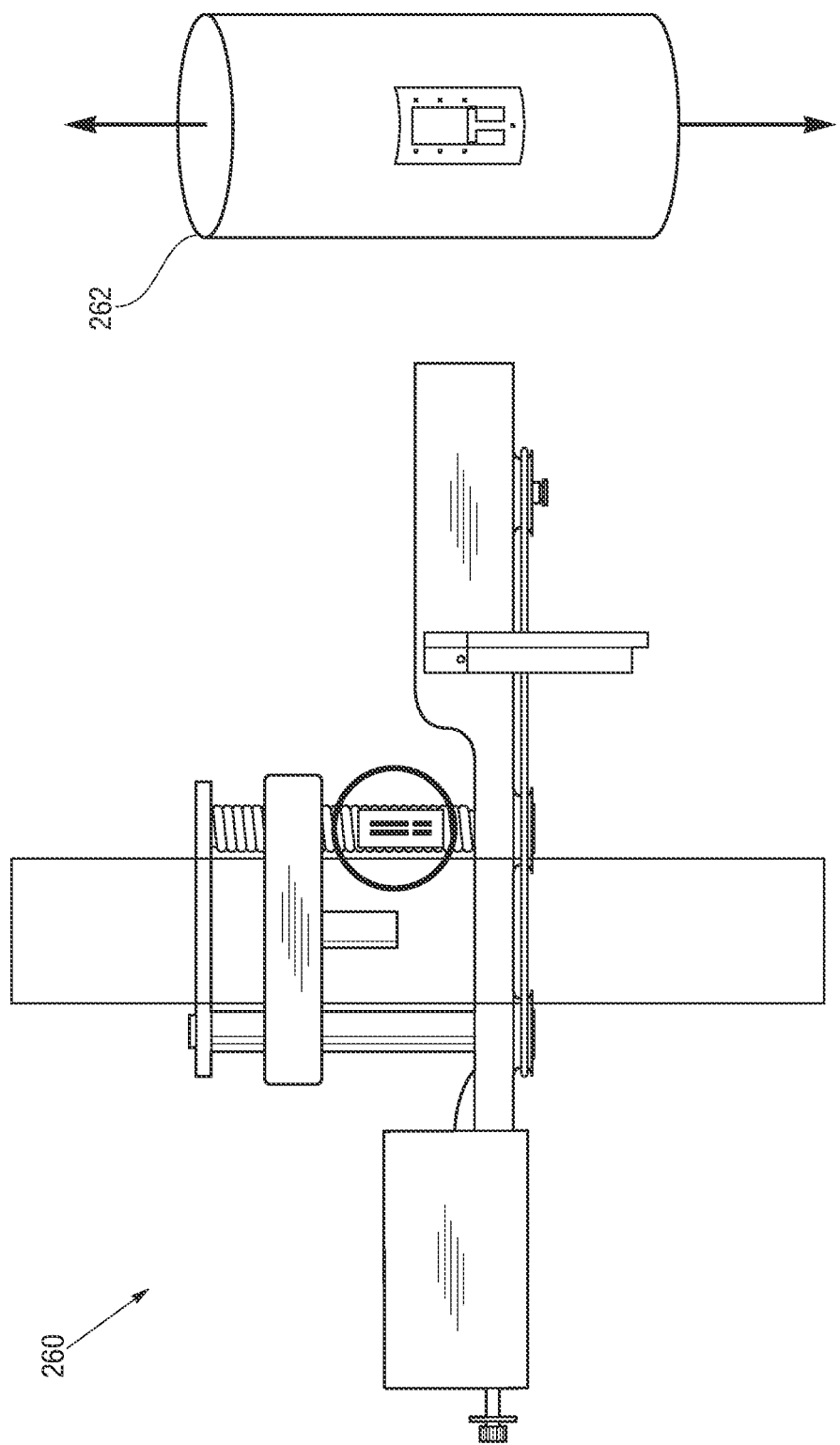
FIG. 8A illustrates the position of an embodiment of a strain gauge on the device.
FIG. 8B illustrates the strain gauge on the unthreaded portion of the rod and the tension forces which it will measure.

A push-pull pulley system 250 can be operable by a push-pull pulley system on the bottom of the base 202, as shown in FIG. 7. On the bottom of each threaded rod 252 is a rotatable pulley. The proximal end of the bottom of the base also contains a pulley. One nylon cord wraps around each of the pulleys. When the proximal pulley is turned, both drive rods will rotate with the same strength. The cord is made out of nylon because it is radiolucent allowing for it to not interfere with imaging as the cords pass under the imaging section. Nylon is strong and will not stretch as the pulley is operated.

A force measurement system 260 can include, on the unthreaded portion of one of the drive rods, a strain gauge, that can be placed as shown in FIG. 8A. This can measure the tension in the rod and can be doubled to account for the other rod, as shown in the diagram in FIG. 8B.

The cylinder 262 shown in FIG. 8B is a view of the unthreaded portion of the rod and the arrows represent the tension forces on the rod, which the strain gauge will measure. The strain gauge will be connected through a DAQ box to filter and amplify the resistive signal and convert it to a force output. This provides real-time feedback for the force present in the mechanism and applied to the patient.

Various loading types, including compression, tension, bending, and torsion can be applied to the subject bone. The types of loading can be evaluated on the following criteria: ability to open up the healing fracture enough to produce a detectable displacement in order to evaluate how much the fracture has healed, ability to apply a repeatable load to the healing bone, and a method of loading used which is non-damaging to the healing bone. It is imperative that the device does not further damage or deter healing of the patient, and that the device supports complete and quicker fracture healing. In some embodiments, loading can be achieved using an expandable member, such as an inflatable balloon as described above, with a pneumatic or hydraulic system that can be adjusted manually or electronically.

Designs using both tension and bending can be used since these loading types meet the criteria described above. Both methods of loading can be able to open the fracture enough to detect a displacement and apply a repeatable load to healing bone. Since bones are stronger in tension and bending in comparison to torsion, a higher force could be applied without damaging a healing bone. Furthermore, tension and bending loading types would be able to apply a direct load to a transverse fracture, the most common type of Colles' fracture.

Various potential loading mechanisms can be used, including but not limited to a worm screw, a rack and pinion, a linear spring, a wave spring, and a pulley.

A worm screw works by rotating on a 90 degree angle on a shaft, and this mechanism transmits motion and power at various speeds and speed ratios. A worm screw can operate smoothly, occupy little space, and can produce a high amount of torque.

Worm screws are also easy to make non-backdrivable, which means that the mechanism can be loaded and the resulting internal forces will not cause the mechanism to return to the initial state. This works for maintaining static loading and mechanism stillness during imaging. Disadvantages of worm screws include: they can have high power losses, and can have a lower efficiency due to considerable sliding action and friction from surface area contacts, but this does not effect the device as the goal is not to transmit power efficiently but to reliably apply static loading. A screw drive operates similarly to a worm screw, and it works by translating rotational motion of the threaded rod into linear motion of the threaded nut.

A device that is similar to a worm screw, though usually less stable and fine in adjustment, is a rack and pinion. In this device, the pinion (circular component) is spun and the rack is moved side-to-side.

A rack and pinion mechanism can be compact, robust, and provide good control over the amount of force that is applied. A high rack pinion device can require high forces to operate when the friction is too high. This device also relies on creating a significant force between the two components which can be challenging in light-weight mechanisms.

Another device that can be utilized to generate a tensile force is a spring. In a spring, an object is deformed by a force and it can return to its original shape after the force is removed. Types of springs include wave springs and coil springs. Wave springs can offer space savings by reducing the spring height, and can apply a wide range of forces and are cost effective.

However, wave springs do not produce a uniform load distribution and can be used with a force spreader plate. Similarly, coil springs can be inexpensive, since they are made of steel and other low-cost metals, and offer a more uniform load distribution in comparison to wave springs. However, coil springs are larger than wave springs.

Another device that can be utilized to produce a tensile load is a pulley, which allows a cord to transmit force around a wheel's circumference.

A pulley can be used to apply a tensile force in any direction. A pulley can have a significant amount of compliance when loaded, especially compared to the other methods presented. They are also only able to provide a pulling force, not pushing and pulling as the other devices.

Space restraints can also be considered for the loading mechanism. For the space constraints, the device needs to fit with an imaging device. For example, a CT scanner can have a height of 7.5", a length of 31", and a width of 5.5".

Another measure to be considered in evaluating the loading mechanisms can be the range of force because the device can apply a range of forces to quantify the degree of healing. For example, the range of force required is between several newtons to 550 Newtons. A linear spring, rack and pinion, and screw drive can produce tensile loads within the entire force range for early and intermediate fracture healing. The wave spring and pulley mechanisms produce a more limited range of forces and may have difficulty in providing the range of forces needed for intermediate fracture healing.

The ease of use of the loading mechanism was also considered. The linear spring and screw drive mechanisms can operate smoothly and can require less effort to operate. In comparison, the rack and pinion, wave spring, and pulley can be more difficult for the technician to apply the same amount of force during operation.

Another requirement considered is that the loading mechanism can allow for fine adjustment, which means that the technician or physician who is using the device can be able to change the force in reasonably small intervals.

The next requirement considered was rigidity, which refers to whether the device is able to remain still and dimensionally stable when a mechanical load is applied. This metric is fairly important because the device desirably remains rigid enough to be stable and motionless during loading to prevent motion artifact in the scanner image.

An additional need is whether the loading mechanism will allow the device to be cast compatible.

Various mechanisms for loading can be used, and various methods can be used for grasping the hand and the distal and proximal ends of the elbow during tensile loading. In some embodiments, the distal and proximal ends of the radius would be potted in resin and the bone would be subjected to tensile loading in an Instron machine to apply easily measurable forces and determine the strength in the fractured region. It is necessary to apply loads to the radius through the patient's skin, soft tissue, surrounding bones, and joints. These tissues have a large degree of variability in geometry, movability, compliance, and pain tolerance, which can be considered.

It is more difficult to grasp the hand than the elbow because the cast can be present, and the fingers and metacarpals have a large degree of movability. It is desirable to apply force through as few joint capsules as possible to minimize the risk of injury and reduce slop in the loading environment, which can negatively impact loading repeatability.

For the tension design, the hand and/or fingers can be grasped and a degree of connection can be applied sufficient to securely transmit high forces (550 N), but not sufficient to cause harm to the patient. Various mechanisms can be used to grasp the hand, including but not limited to a Velcro brace on the fingers, athletic tape on the fingers, or an under-cast tightenable grasper.

In some embodiments, a Velcro finger brace uses Velcro as a fastening method to secure a brace made from soft/elastic fabric, such as felt or neoprene, around the fingers and/or hand. The Velcro finger brace can provide ease of use, high adjustability, and good patient comfort. However, it presents some challenges with reproducibility of loading due to the mobility of the fingers and the need to load through multiple joint capsules in the fingers, hand, and wrist.

The brace can also include the addition of soft foam and plastic supports to the inner and outer portions of the hand The plastic supports can be formed from a variety of materials, including Thermomorph Plastic Pellets.

In some embodiments, an under-cast tightenable grasper can be used, and can include thin plastic staves, connected by cording, that are inserted under the cast along the skin. The cord can be tightened in order to produce circumferential compression on the hand. This technique relies on producing sufficient compression to prevent the grasper from slipping off the hand in tensile loading. The under-cast tightenable grasper can be able to apply a load through joint capsules in the hand and wrist.

Various requirements can be considered in relation to the hand gripping mechanisms including, but not limited to, security, patient compatibility, ease of use, cast compatibility, cleanability, and cost effectiveness. Security refers to the effectiveness of the gripping device in properly restraining the hand. as the gripping mechanism needs to keep the hand in place while an external load is applied to the fracture. Additionally, patient compatibility refers to the level of comfort of the hand gripping mechanism.

Another requirement considered was the ease of use of the hand gripping mechanism as the physicians/technicians who are using the device need to be able to apply the gripping mechanism to the patient in a reasonable amount of time.

Another requirement is the cast compatibility, as it would be beneficial for the gripping mechanism to be able to restrain the hand.

The next requirement is cleanability, which refers to whether the hand gripping mechanism is easy to clean. In some embodiments, the device does not require sterilization (since the gripping mechanism is used externally on the patient). It is important to note that sterilization would involve removing all microorganisms from the gripping mechanism, while cleaning the gripping mechanism would simply involve reducing the number of microorganisms. This could be accomplished with standard wipe-down procedures.

Various devices can be used as elbow grasping mechanisms, including but not limited to an elbow brace, blood pressure cuff, and bony contacts for the elbow.

A padded elbow brace applies force to the proximal end of the radius through circumferential pressure on the medial and lateral surfaces. These braces can be easy to fit and comfortable, are easily cleanable, and skin friendly. Furthermore, elbow braces, such as the brace shown in FIG. 3, can come with adjustable straps, which allow for a custom fit.

It is possible that an elbow brace may need additional security while a mechanical load is being applied to the patient's fracture.

A second elbow gripping mechanism is a blood pressure cuff. A blood pressure cuff can be relatively comfortable and easily cleanable. Furthermore, blood pressure cuffs are relatively affordable, and they can fit a variety of elbow sizes (similar to an elbow brace).

Figure 10:
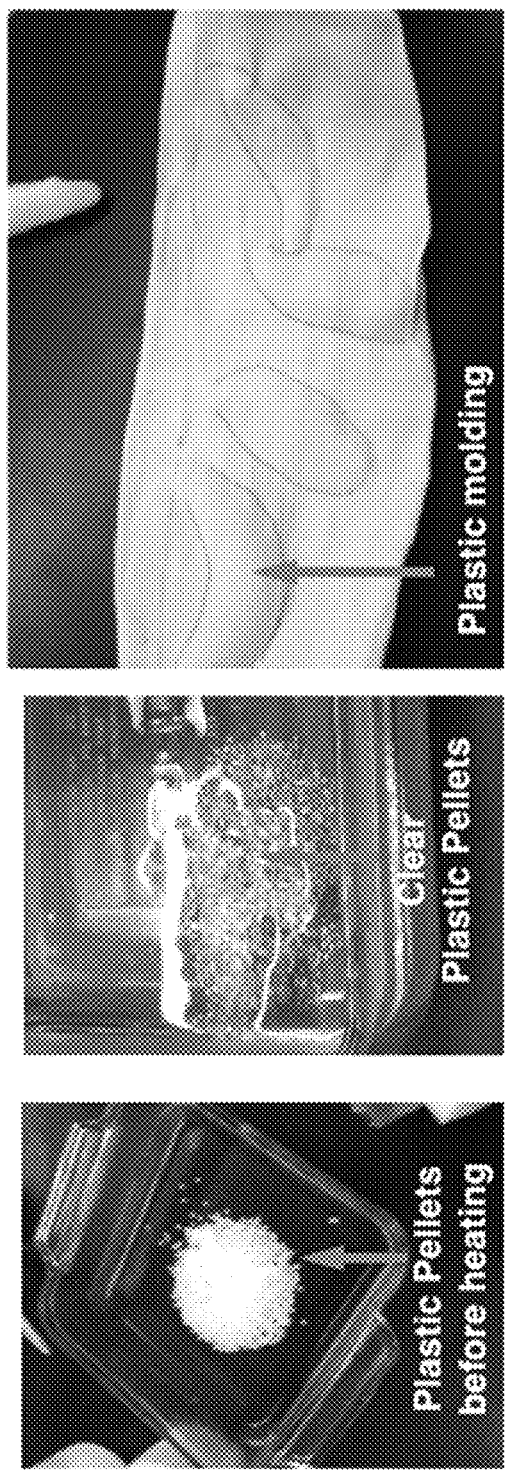
FIG. 10 illustrates a sequence of steps followed in developing bony contacts.

Another elbow grasping mechanism is bony contacts. To develop bony contacts, various materials, such as Moldable Plastic Pellets from Thermomorph, can be used. In some embodiment, the elbow contacts can be formed by pouring the plastic pellets into warm water, as shown in FIG. 10, and waiting until they turn clear and stick together. The water is removed and the plastic is molded. Components are placed on an elbow using the guide of an articulated skeleton to provide extra pressure near where the bones were palpable from the skin's surface. The pieces were then held together using athletic tape to make a brace insert.

Bony contacts (plastic molding) can provide improved comfort and security to the patient, while a mechanical load is being applied to the fracture. The goal is to apply loading more directly to the skeletal structure. Localized pressure points also reduce the cut-off of circulation and other compression points that caused tingling and cold fingers in other designs.

Tensile Design

Figure 11:
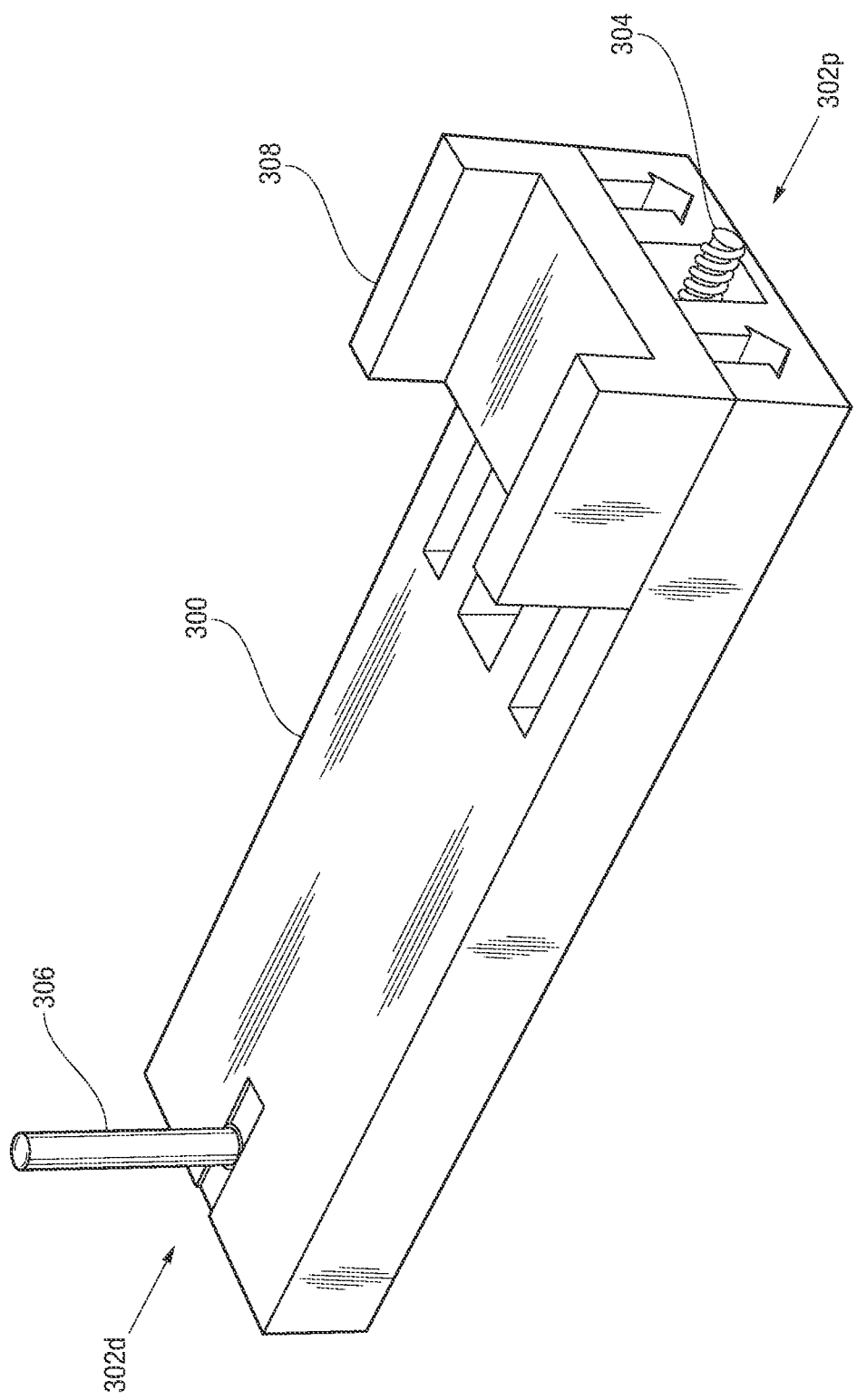
FIG. 11 illustrates an isometric view of an embodiment of an initial tensile loading design.

An embodiment of a tensile design is shown in FIG. 11. This design uses a worm screw for loading, which fixes the hand and moves the elbow. The basis of the design allows for interchangeable gripping options.

The embodiment shown in FIG. 11 includes a base 300. The base 300 can have a variety of shapes and sizes, but in some embodiments the base can be 15 inches in length by 4.5 inches in width and 1.5 inches in height. It can be in the form of a rigid rectangular platform that can house support for the arm and loading mechanism. A proximal end 302p of the base 300 can include a large rectangular cut out in the middle, which allows for the worm screw to pass through. On either side of the worm screw are two T-slotted tubing slots, which use an arrow-shaped design to allow for better stability. At a distal end 302d of the base 300, there is a slit for insertion of the hand restraint peg. FIGS. 12A-12B depict the top and isometric views of the base 300.

The loading mechanism 304 is in the form of a worm screw. The worm screw can be seen inserted into the base as shown in FIGS. 12A-12B. The worm screw can be attached to the base inside the hole on the inner side of the cutout and can fit within the cutout.

The device also includes a gripping mechanism 306 in the form of a hand peg, which is shown in FIG. 13. The hand peg is in the form of a cylinder that can vary in dimension, but in one embodiment the hand peg is 1 inch in diameter and 3 inches in height.

The hand peg can be covered in a thin padding to allow for the fingers to comfortably wrap around, which will aid in gripping the hand in a repeatable manner and location. In some embodiments, the hand peg can be removable to allow for adjustability. The removable peg can aid in ease of preliminary printing and could allow for an interchangeable gripping mechanism if desired. The hand can be secured to the peg through the use of a Velcro finger or athletic tape strapping as explained above.

Various other mechanisms can be used as a gripping mechanism 306. In some embodiments, the gripping mechanism is in the form of a circular or half-circular hand rest to allow the patient to stabilize their hand and the area proximal of the bone fracture. In some embodiments, the gripping mechanism is in the form of a bar such that the patient can wrap their fingers therearound for increased stability of the area proximal to the bone fracture.

Figure 14A:
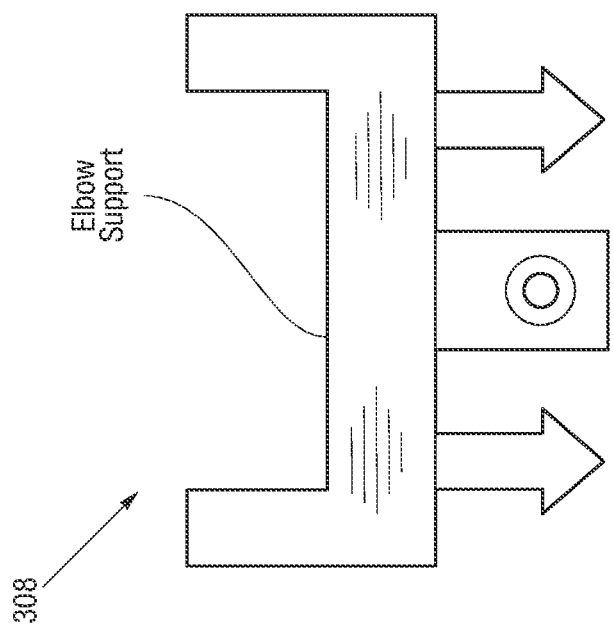
FIG. 14A and FIG. 14B illustrate an isometric and front 2D view of the elbow support shown in FIG. 5.
Figure 14B:
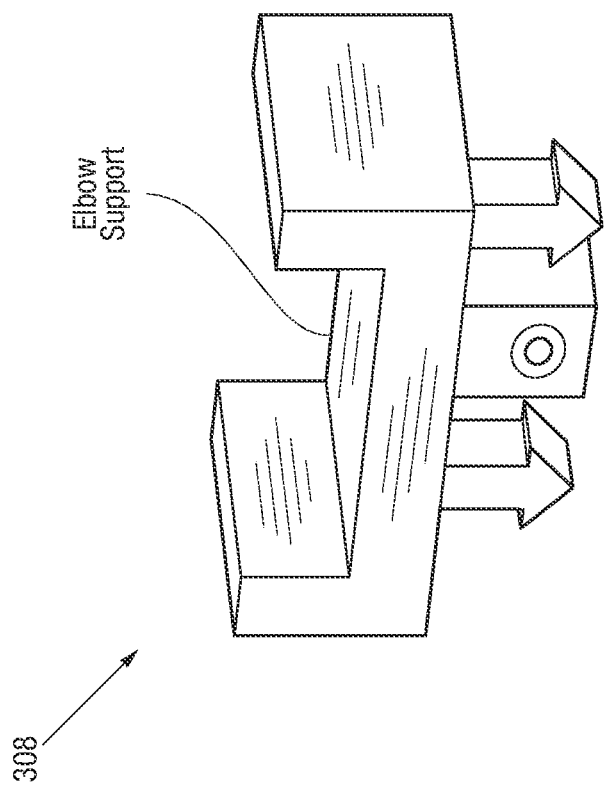

The device also includes a proximal support 308, such as an elbow support slide, which is shown in FIGS. 14A-14B. A forearm/elbow can rest within the elbow support.

The bottom side of the elbow support can include T-slotted tubing inspired arrow shaped sliders, which will fit snugly into the slides. The middle rectangular extrusion contains a threaded hole, which is where the worm screw can be fed. This can allow the elbow support to be moved via the worm screw within the sliders. The elbow can be affixed to the slider through the attachment of a semi-rigid elbow brace to the top of this piece.

Tension Design

Figure 15:
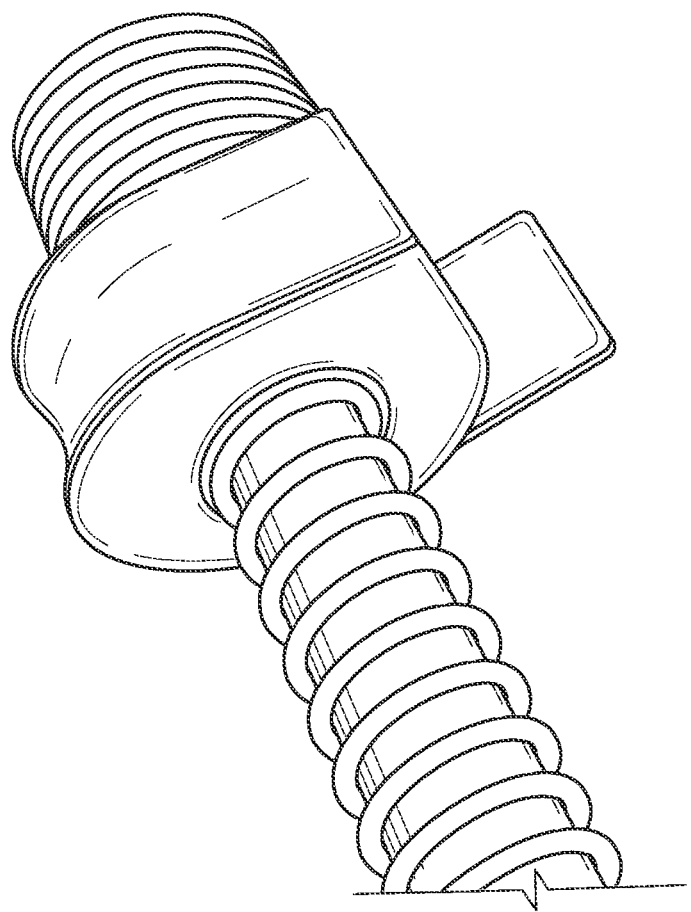
FIG. 15 illustrates an exemplary schematic of a screw drive mechanism.

In some embodiments of the tension design, the device needs to apply an adequate tensile force in order to sufficiently displace the bone. To achieve this force, the loading mechanism utilizes a screw drive, composed of a rotating threaded rod and a translating threaded nut, similar to the one shown in FIG. 15.

Figure 16:
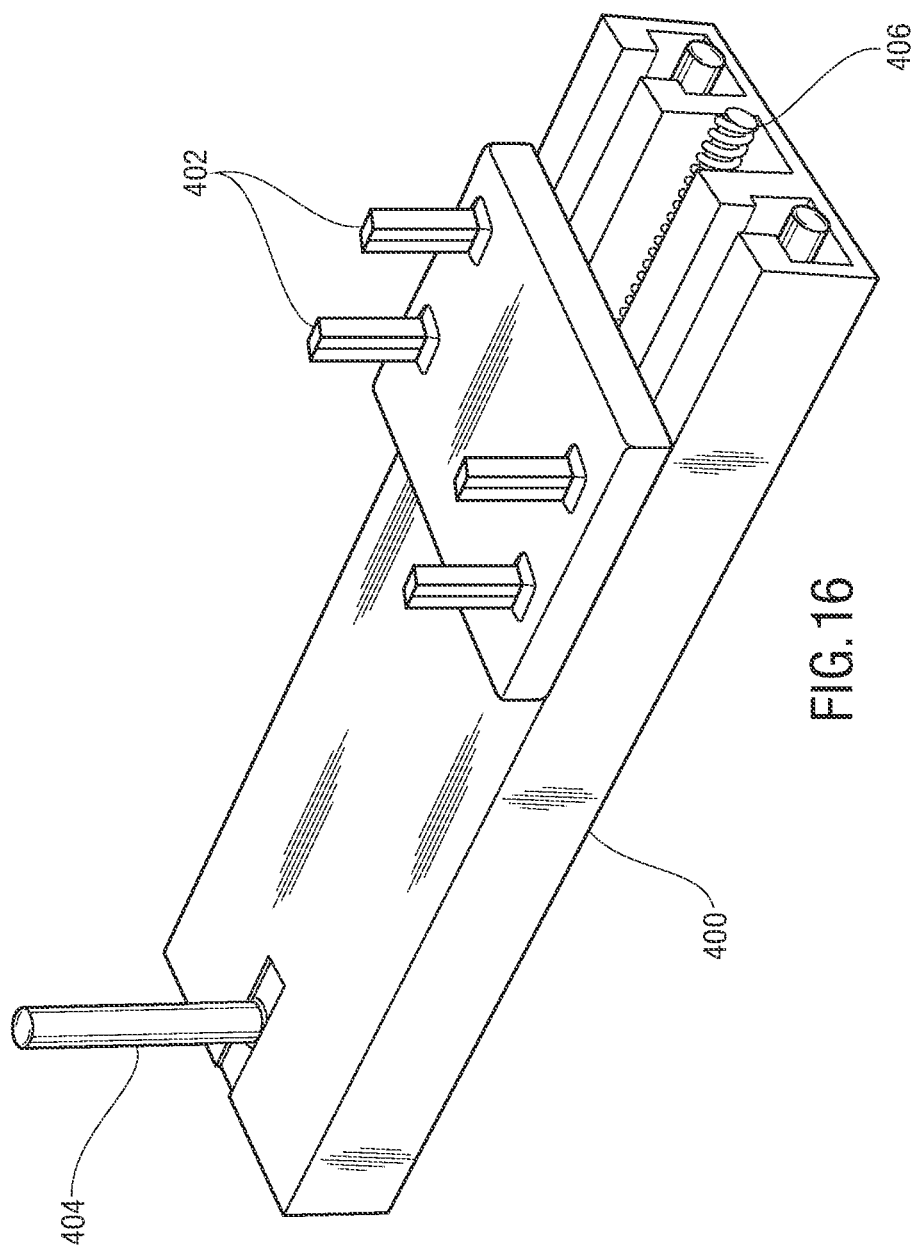
FIG. 16 illustrates a CAD model of an embodiment of a tension design.

This mechanism works by rotating on a shaft to produce linear translation. A screw drive allows for both high force and high precision tensile loading to be applied to the patient's distal radius fracture. As seen in FIG. 16, an embodiment can include a base 400, a proximal support 402 in the form of an elbow/forearm support, a distal support 404 in the form of a hand peg, and a worm screw 406.

In the tension design, the base keeps the device stable and houses the elbow support, hand peg, and worm screw. The elbow support allows the patient to rest his/her elbow, and the support is moveable via the worm screw. A plurality of attachment pegs can be associated with the elbow support, which allows an elbow gripping mechanism to be attached. Similarly, the hand peg is the location where the patient can comfortably secure his/her hand while the screw drive will apply the tensile force.

In some embodiments, drawer slides can be utilized instead of the guide rods for ease of manufacturing and known reliability. One drawback of this design that we noticed after building was the difficulty to operate the screw drive in between the drawer slides. The elbow slide contains screws to serve as the gripping mechanism attachment peg.

Side-Application Bending Design

In some embodiments, the device has a bending application. The bending design uses a mechanical advantage to apply higher internal bone forces and higher fracture displacement than the tension design without damaging soft tissue. This permits the imaging of incomplete and complex fractures.

Figure 17:
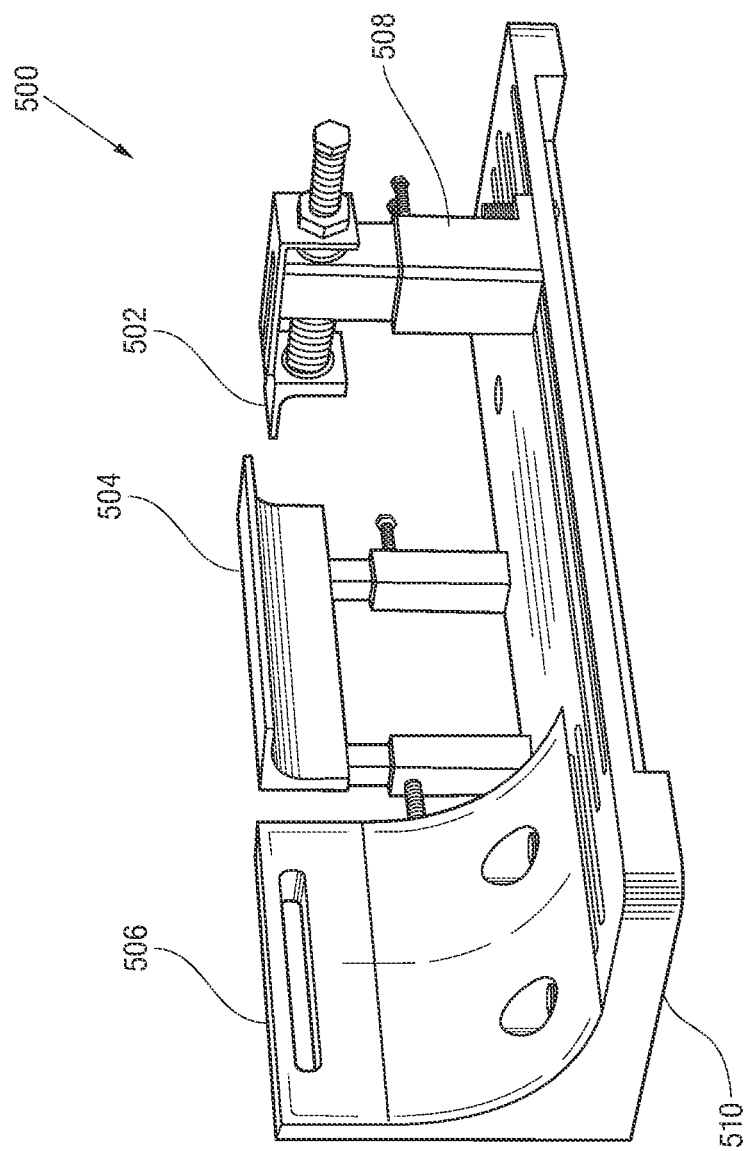
FIG. 17 illustrates an embodiment of a design utilizing bending.

An image of an embodiment of a fracture testing device 500 is shown in FIG. 17. This device 500 functions through the force application by a spring of a known stiffness constant k, and the force is applied through a rod to the styloid process and head region of the radius. Furthermore, a platform holds the forearm, and side walls and strapping slots are designed to stabilize the arm.

This device can be right/left compatible through a process of switching the force application and arm restraint pieces to the opposite side and reattaching them to the base with screws.

The device 500 of FIG. 17 includes a force applicator 502 that applies the force to the fractured bone by pressing against it through the use of a spring of a known constant K. The wrist is lined up with the edge to ensure force application is in the same location every time. The arm is held in place with a support 504 and it is adjustable for multiple arm sizes through vertical movement. The ledge is pressed down onto the exposed radius portion of the arm in order to hold it in place. A support 506 is used for the proximal end of the forearm. The slit on the top allows for a strap to be attached to better secure the arm in place. A force applicator base 508 is used for the force application spring, which is adjustable on all three axes. A base 510 supports the device 500, which increases device rigidity, and serves as a resting spot for the arm and wrist. The various slots allow for the three moveable parts (parts 1-3) to be moved along the slots to adjust for different arm sizes. The pieces can also be switched to the opposite side for right and left compatibility.

The device of FIG. 17 can also include padding and Velcro strapping, as well as adjustments to sharp corners and straight lines. This will allow the device to better accommodate the organic shape of the forearm and improve the user experience. User comfort is also important to maintaining stillness and image clarity in an imaging device. An ergonomic design leads to a clearer image and better information for the physician to guide treatment.

Various design aspects are related to the device of FIG. 17, including: 1. Ergonomics—This device can be made to comfortable to the user and to accommodate various arm sizes. This could be improved by rounding out some of the rectangular aspects, removing sharp corners, and adding padding to the design. 2. Slack/Deflection—The slack in the components of the device can be varied. 3. Right/left changeover—The device can be changed from the right to left arm setup by moving and fastening the components into place while keeping all pieces together. Other methods can be used to switch between right and left configurations, including the use of two separate devices or decreasing the amount of moving parts by changing the forearm restraint to be conducive to both right or left arms without alteration. 4. Spring constant determination—In some embodiments, the spring is a radiolucent ceramic spring. The spring can be replaced by different mechanisms or springs that have appropriate spring constants. 5. Arm security—The device can include slots which could be used to add a forearm strap to aide in restraining the arm in place very securely or repeatedly. An elbow brace, inflatable pressure cuff, or a similar method could be used to restrain the forearm. A strap can be added to restrain the hand as well. Motion can be limited to avoid having motion artifact in the CT scanner image.

As mentioned above, limitations in the previous bending design may include: ergonomics, slack in measurements, slow right/left changeover, spring constant determination, and arm security. In another embodiment of the bending design, described below, alternative mechanisms can be used to apply a bending force, including but not limited to using a lever, 3-point bending, and a screw drive.

Design Evaluation for the Bending Design

Figure 18:
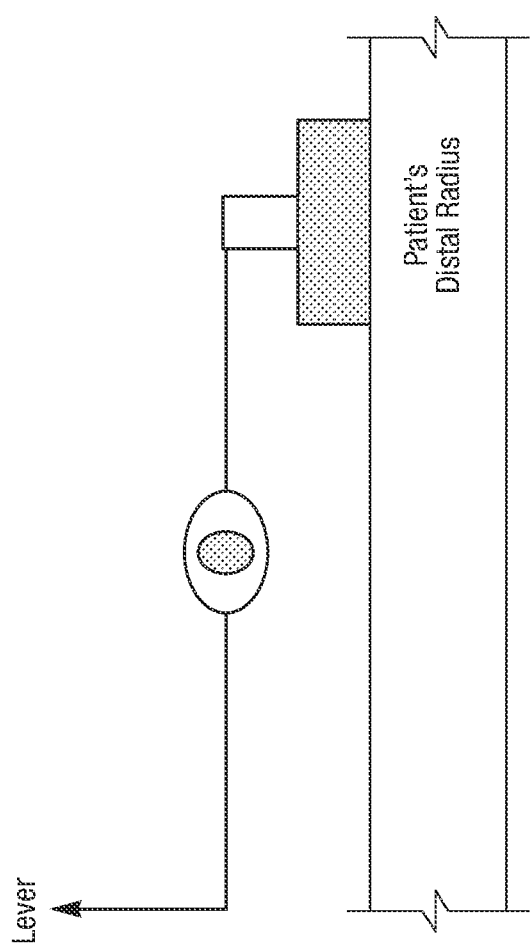
FIG. 18 illustrates an exemplary bending design utilizing a lever.

The use of bending as a method to apply a mechanical load can include the ability to open a healing fracture and can apply a repeatable and non-damaging force, although additional features may be needed for patients that are wearing a cast. FIG. 18 illustrates an embodiment of bending design that utilizes a lever.

A lever is a mechanism that consists of a rigid bar that rotates about a fixed point (known as the fulcrum) in a lever mechanism, force is applied to one end of the lever, and the object to be moved is usually located at the other end.

A lever system in the bending design allows for a reduction in the amount of force needed to move a load. However, disadvantages of lever systems include: there can be significant wear near the fulcrum point (which reduces the mechanical advantage and leads to inefficiencies in the system), and lever systems involve quite a bit of moving parts (which can reduce the reliability of the applied load).

Figure 19:
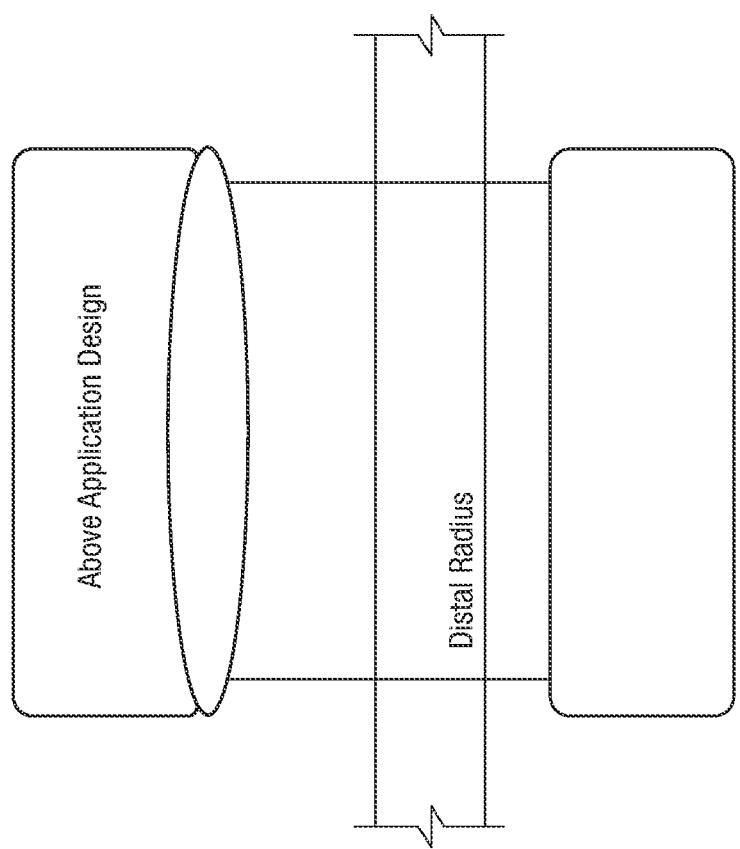
FIG. 19 is a side view image of the bending design that can apply a load from above the point of application. In this image, the patient's right hand is facing down.

Another embodiment of a bending design is shown in FIG. 19. This design would apply a bending force from above the distal radius fracture.

Similar to the other bending designs, this design is can use a mechanical advantage to apply higher internal bone forces than the tension design without damaging soft tissue. Additionally, this loading mechanism would be able to apply repeatable bending forces, would occupy less space, and would maintain stillness during loading.

Figure 20:
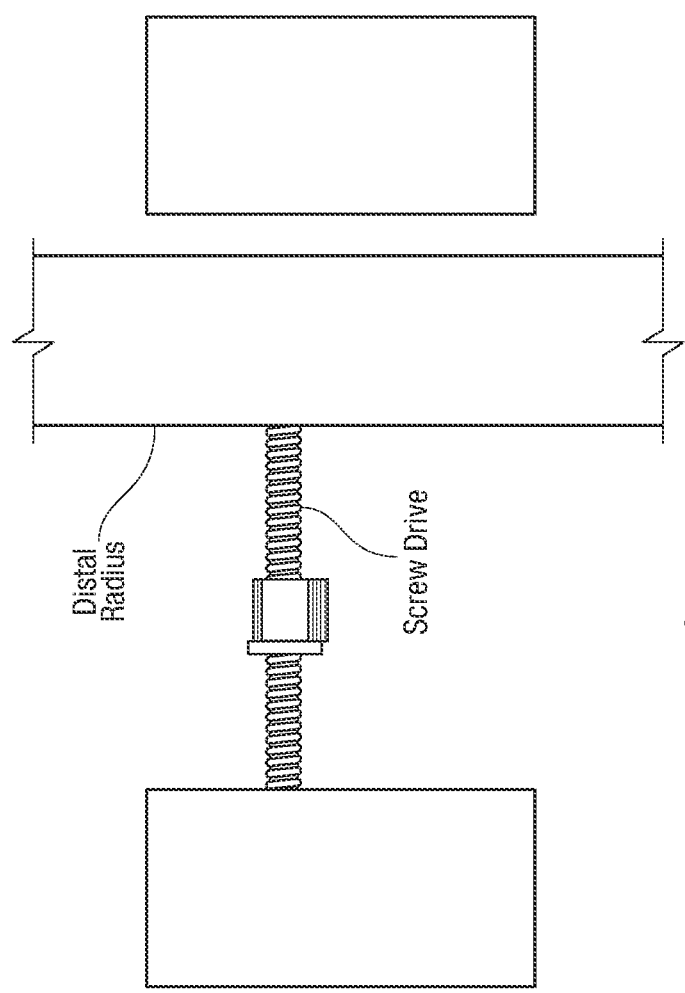
FIG. 20 is a drawing and schematic of a screw drive design to apply a bending force.

Another embodiment of a bending design uses a screw drive, as shown in FIG. 20. A screw drive is quite similar to a worm screw, and it operates by translating rotational motion into linear motion. Similar to a worm screw, screw drives can occupy less space, are cost effective, and operate smoothly and quietly. Furthermore, they can produce a wide range of forces and apply a repeatable force.

Other design requirements include ergonomics and the design's radiolucency. Radiolucency can be important so that at least a portion of the device is transparent to X-rays.

In terms of reliability/repeatability, the screw drive and design that applies a bending force provide good control over the amount of force that is applied.

Another design requirement is fine adjustment of the loading mechanism (meaning a user can change the force in reasonable intervals). For example, the screw drive design can provides good control over the amount of force that is applied. The lever design can have moderate fine adjustment abilities.

For device rigidity, the screw drive and application designs can help maintain stillness during imaging and can promote good stability. The lever design is less rigid due to moving parts in the mechanism.

Another feature is radiolucency. The designed can be completely or partially radiolucent, rather than entirely radiolucent without special materials.

Figure 21:
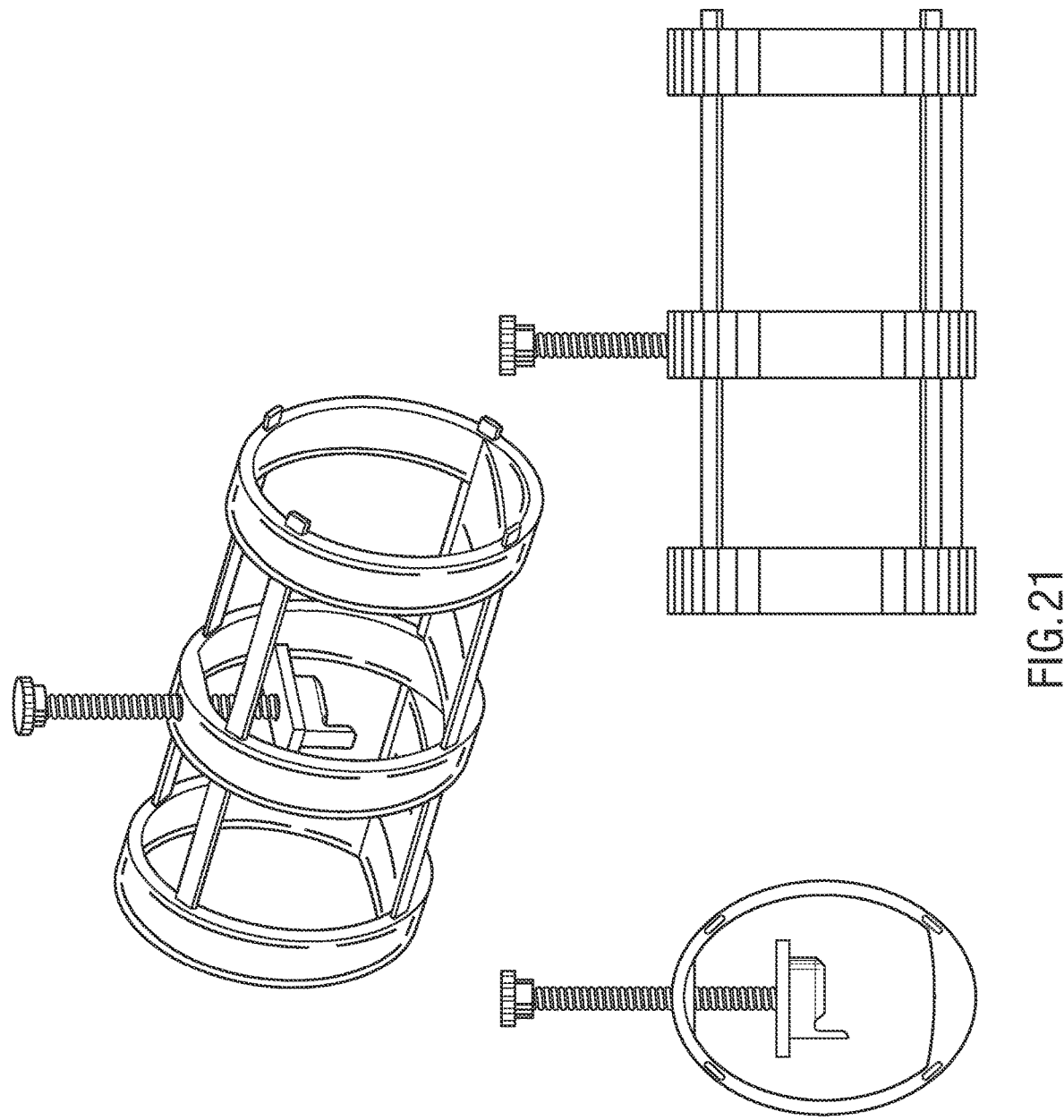
FIG. 21 illustrates a round bending design with single drive screw.

In some embodiments, a design to better accommodate the imaging region of the imaging device or scanner is in the form of a bending design with a round frame shown in FIG. 21. This design is visually more elegant and offers significant materials reductions, however it does not allow for accurate force measurement and experiences significant device deflections in loading.

In some embodiments, a bending force can be applied to the distal radius in order to measure the extent of fracture healing.

Figure 22:
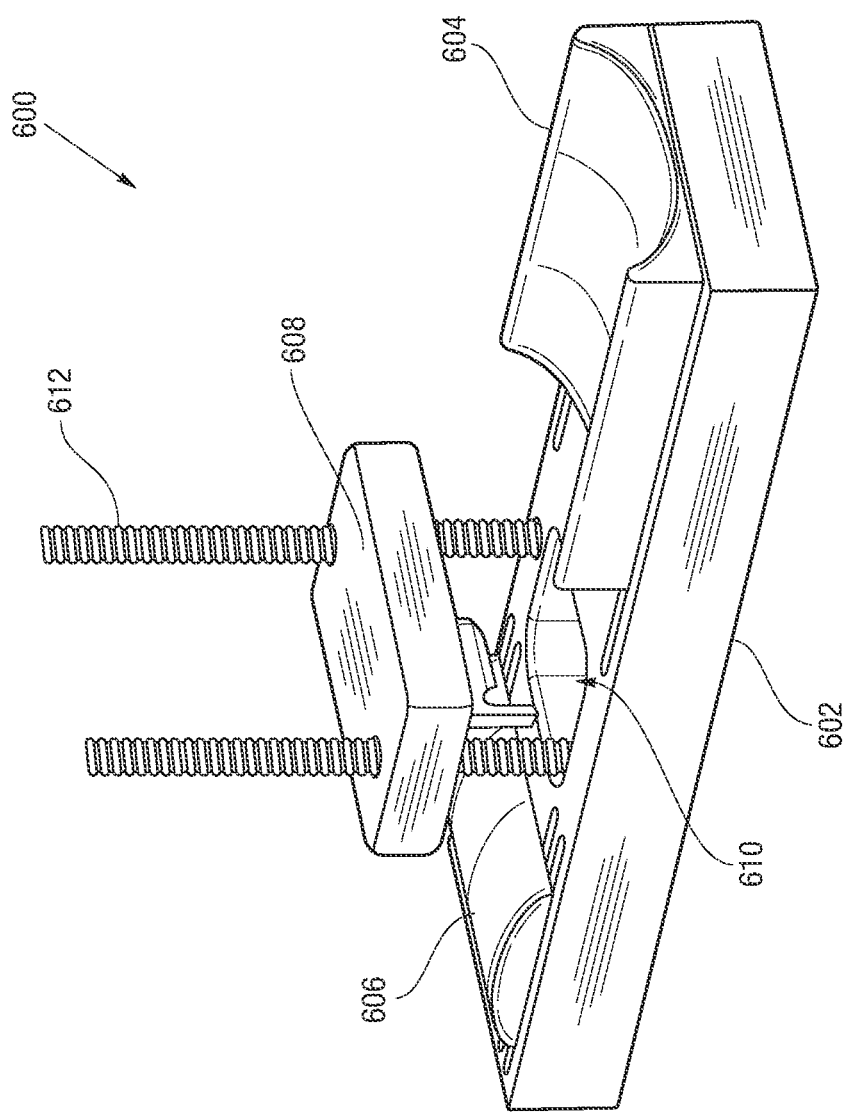
FIG. 22 is a CAD Model of an embodiment of a bending design.

In some embodiments, a 3-point bending force can be applied to the patient's distal radius, as shown in FIG. 22. The bending force device 600 shown in FIG. 22 includes a base 602, a proximal support such as elbow support padding 604, a distal support such as hand support padding 606, a force application component 608, a hole 610, and one or more screws 612. The device 600 can vary in size depending on the size of the imaging modality in which it fits. For example, the device can be sized by using dimensions of the CT bore (7"×31"×5.5"). The device 600 includes the base 602 that holds the elbow and hand supports, and applies a 3-point bending moment to the patient via the force application component.

This bending design can eliminate the instability of the forearm caused by resting the forearm sideways with the thumb facing (for example, by rotating the arm to rest on the palmar surface). The hole is the location over which the patient places his/her distal radius. This design provides the mechanical advantage of reducing the load borne by the screw (by splitting the force between two screws), effectively halving the force and torque needed in operation. Restraining Velcro can be added to secure the arm to the base in an adjustable manner.

The base 602 of the device 600 shown in FIG. 22 can be in the form of a rigid platform that can house support for the arm, elbow, and loading mechanism. The middle portion of the base consists of a cut-out, which is where the bending moment will be applied above. Allowing the force application to follow a three point bend model effectively while maintaining the structural integrity of the device. The slots cut out along the edges of the base allow for the attachment of adjustable Velcro (not pictured) to hold the forearm securely in place.

The elbow support padding 604 can have a circular shape and can allows the patient to rest his/her forearm and elbow. This is meant to increase comfort and ergonomics of the device.

The hand support padding 606 can have a curved shape and can provide support to the hand. It fits the natural curve of the hand to increase comfort.

The force application piece 608 can be attached to the base using a variety of mechanisms, including screw drives. The rectangular support is moved via the screw drives to increase and release the force on the arm. The rectangular boss houses a pressure point piece. This pressure point contains the longer horizontal extrusion with a rounded edge meant to apply force to the radius. Dimensioning for this is based on average sizes of wrists and radius bones and will require more research to verify that the force will not be applied to the ulna directly. The side of the pressure piece consists of a flat piece to be lined up with the styloid process on the side of the wrist to ensure that the load is applied to the same location of the radius every time.

The hole 610 is the location where the 3-point bending moment is applied to the patient's distal radius.

The screws 612 allow the force application piece to move up and down in a measurable manner.

The screws can be formed from a variety of material, including metal, with padding of foam pipe insulation and the pressure point piece being of moldable thermoplastic.

The bending design can be machined out of PLA with carbon fiber reinforcement to ensure radiolucency.

The methods and systems of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1

Figure 23A:
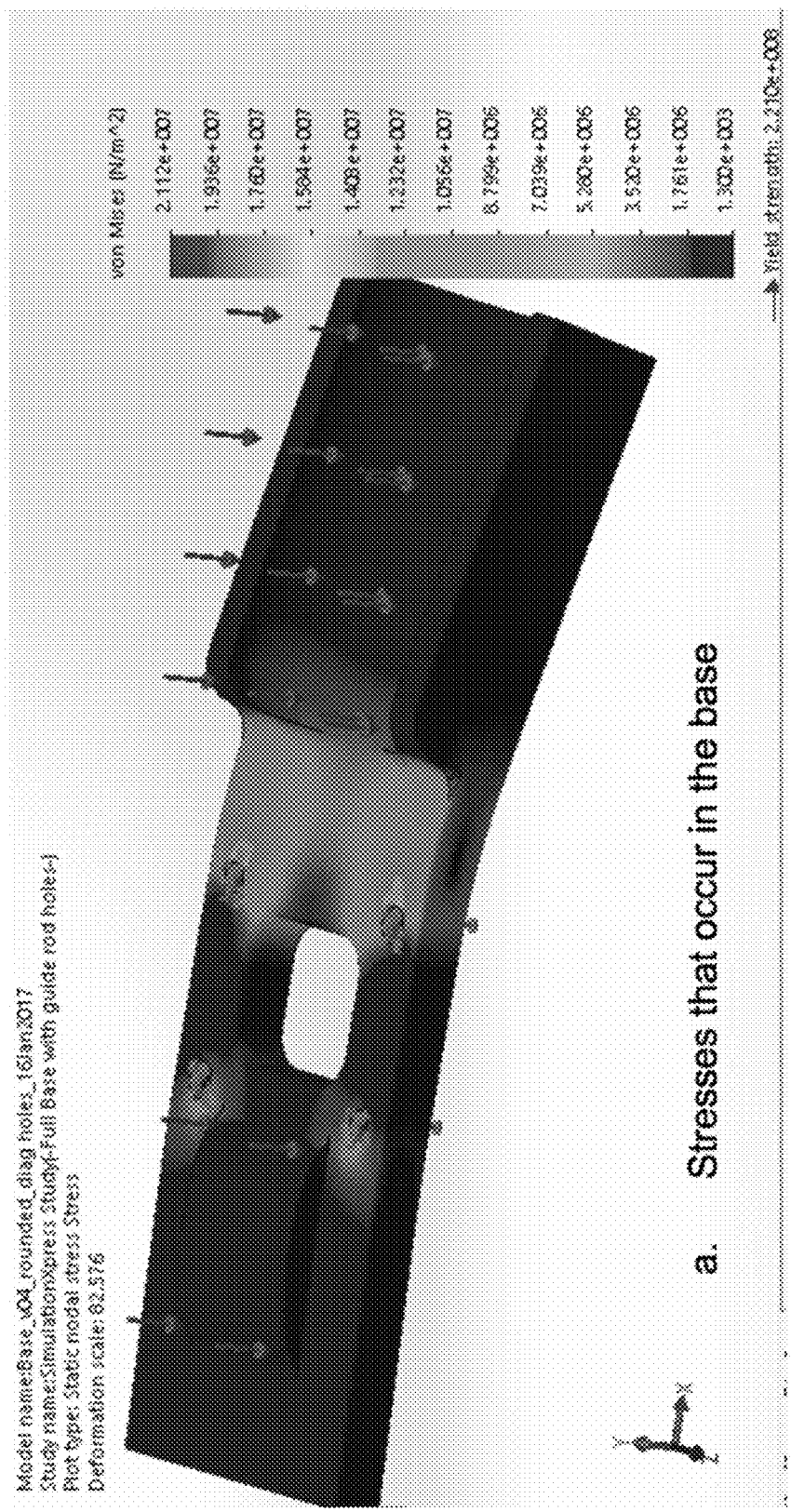
FIG. 23A is an exemplary map of the stresses that occur in the base of the model.
Figure 23B:
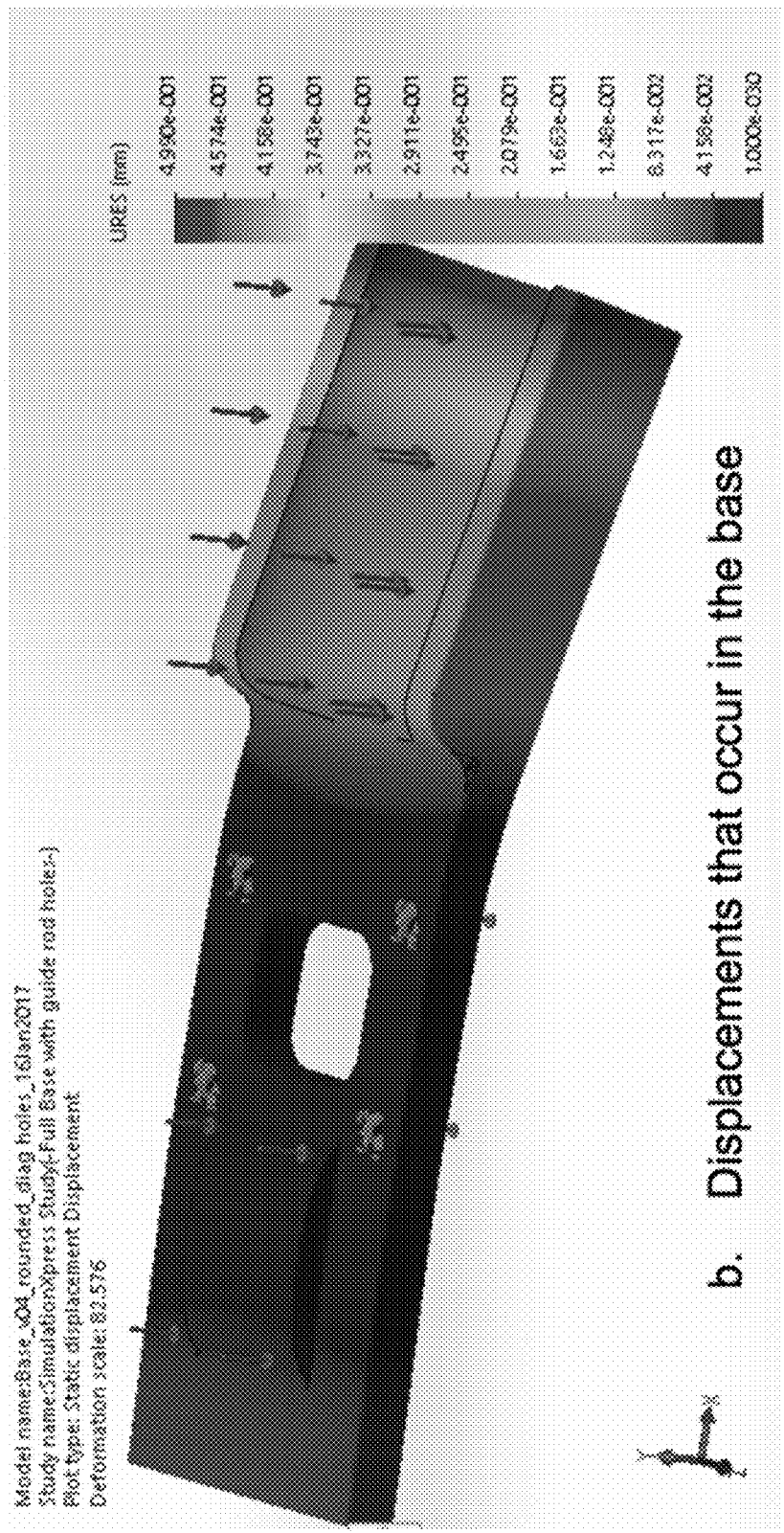
FIG. 23B is an exemplary map of the displacements that occur in the base of the model.

In order to analyze the strength and anticipated deformation of the design, Solidworks Simulation software can be used. Stress analysis was run on the parts along with varying geometry. For these simulations, the threaded rod holes were considered to be fixed in all three axes. The simulations were run with a force of 550 N because this was the max force anticipated to achieve the necessary displacement to diagnose fracture healing levels. Some simulations were run with a force of 550 N total applied while others were run with 550 N applied per face. The further descriptions of simulations describe the force levels applied. Applying 500 N per face is not an accurate representation of the stress values which will be seen but still allows for comparison between designs. Resulting images from the simulations on the standard design of the base piece are shown in FIG. 23A and FIG. 23B. FIG. 23A shows the map of the von mises stress on the part and FIG. 23B shows the displacement of the part.

Figure 24A:
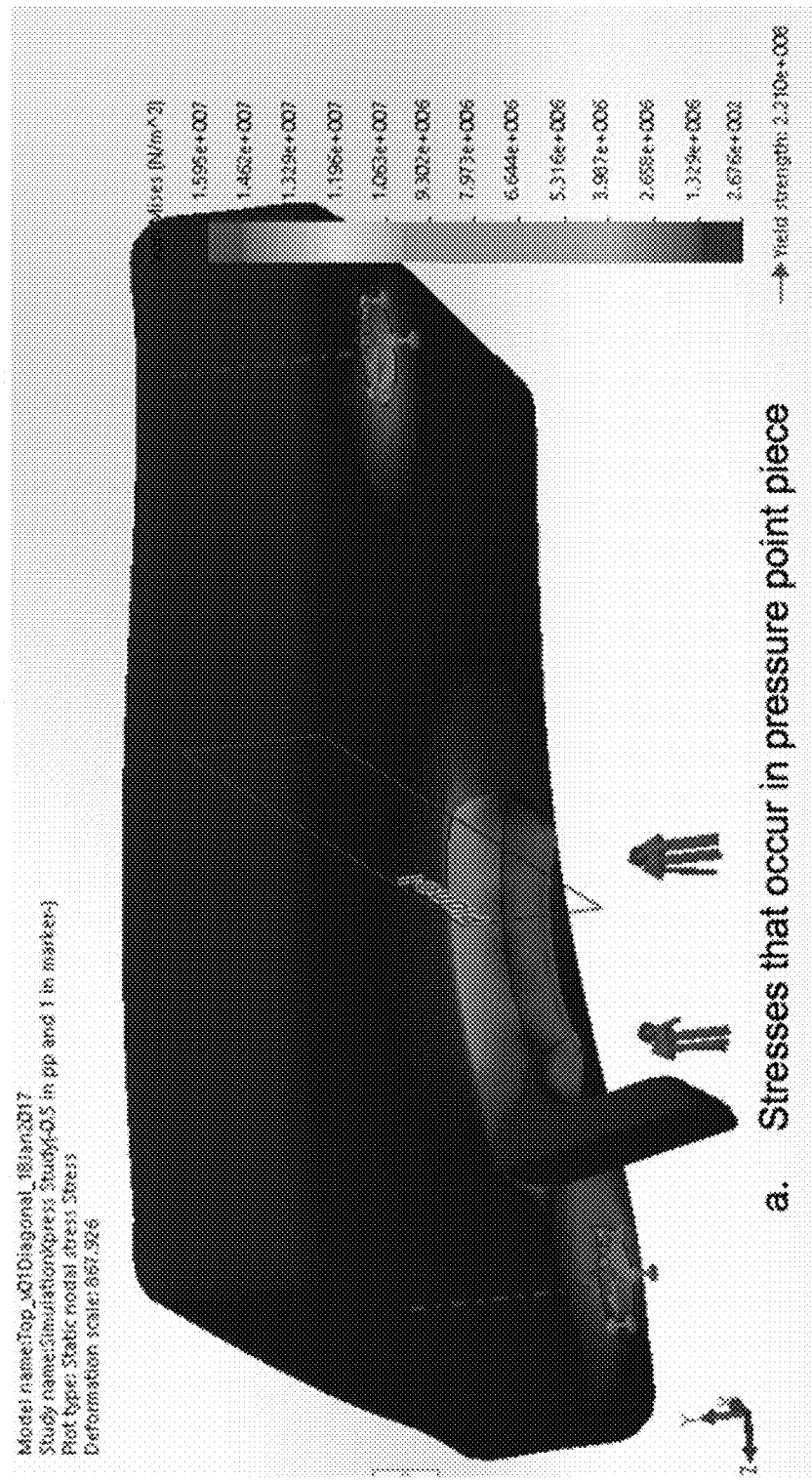
FIG. 24A is an exemplary map of the stresses that occur in the pressure point piece.
Figure 24B:
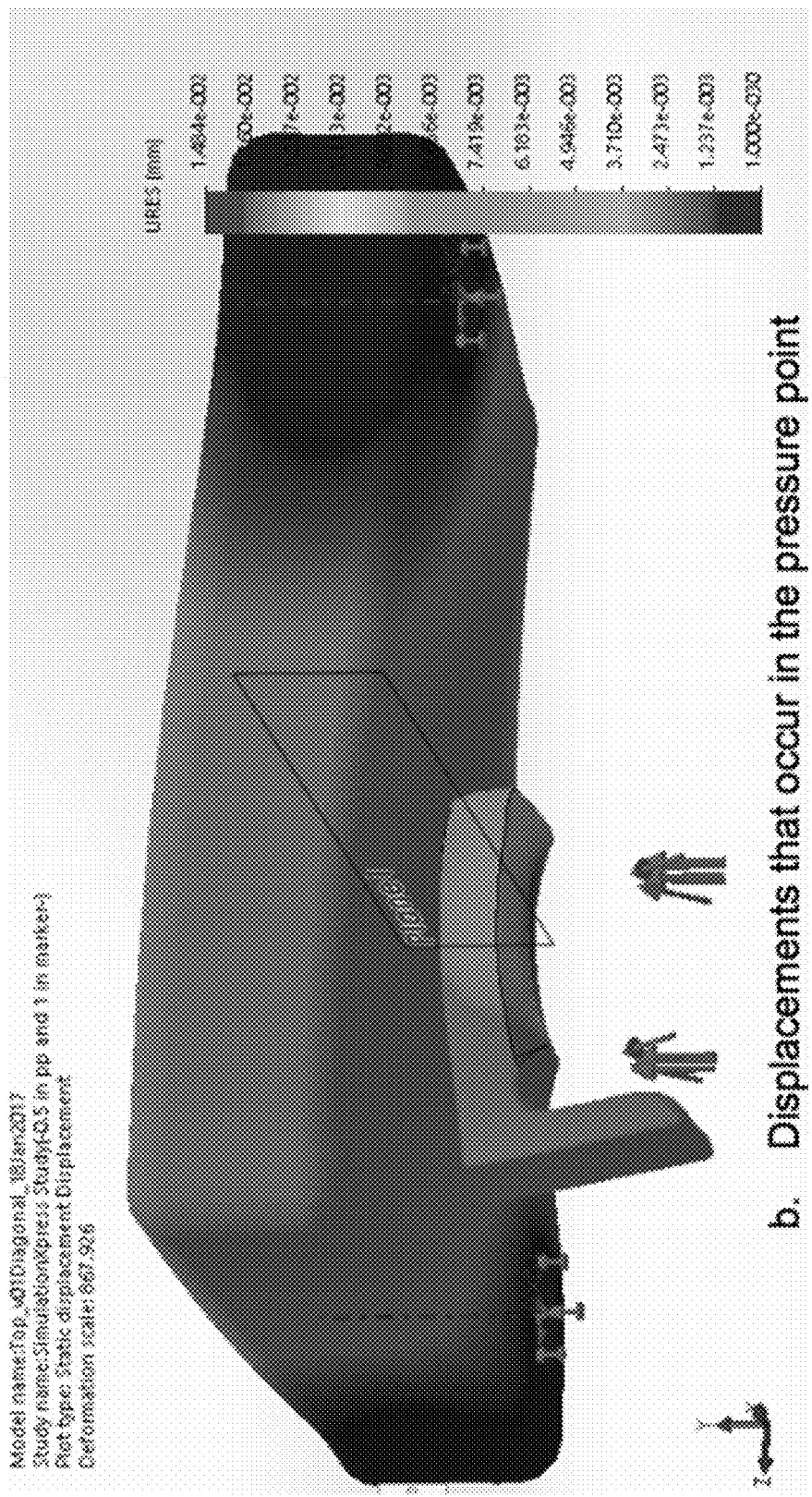
FIG. 24B is an exemplary map of the displacements that occur in the pressure point piece.

The deformation shown in these images is not to scale, as can be seen on the top left corner of the images; this deformation has a scale factor of 82. Some minimal changes on the thickness of the base piece were made, along with comparing simulations of the piece with and without the arm supports. These simulations were found to not be an accurate representation of the behaviour expected in the top piece because they did not take into account forces applied from design additions such as the connection clips to the machine and the Velcro for the arms and the guide rods. Focus on stresses in the device were on the geometry of the pressure point piece primarily. FIG. 24A and FIG. 24B show the stress and displacement values of the pressure point piece. Deformation in these images is scaled up 867 times.

Pressure Point Geometry

Figure 25B:
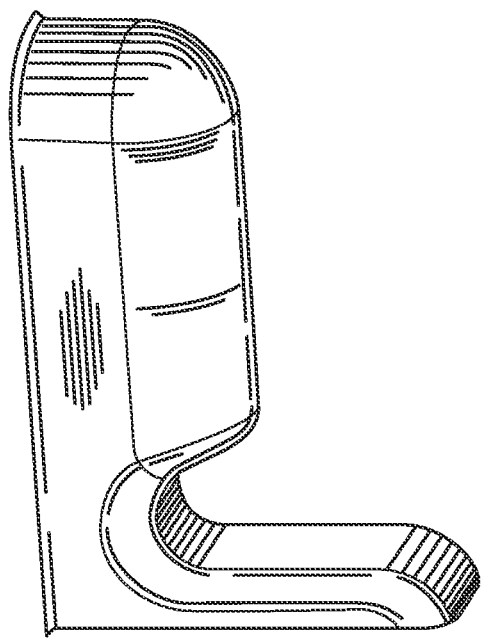
FIG. 25B shows a point that has a chamfered tapering.
Figure 25A:
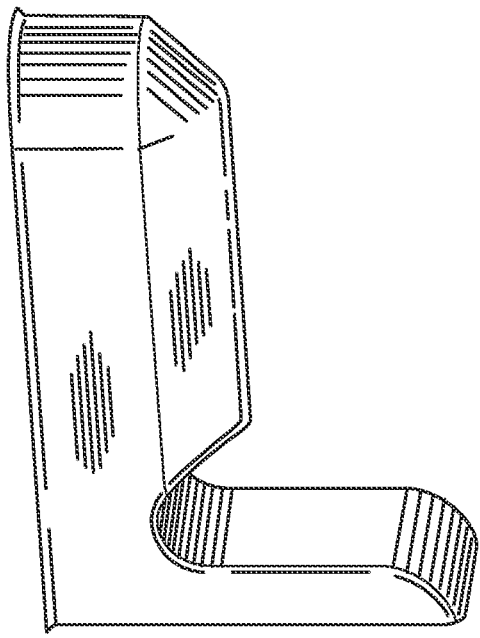
FIG. 25A shows a pressure point with a full round surface.

Several different geometries for the pressure point can be used. In some embodiments, two different shape pressure points can be modelled. One had a full round surface with a radius of, for example, 0.25 inches, as seen in FIG. 25A, and the other had a chamfered tapering off to a smaller face, (resulting in a radius of, for example, 0.12 inches) which contacts the wrist as shown in FIG. 25B.

Figure 26:
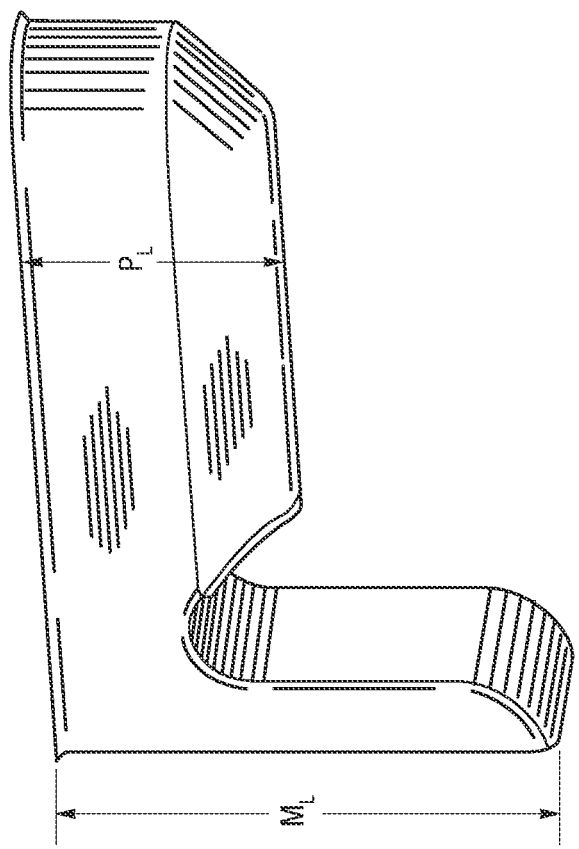
FIG. 26 is an image of pressure point with dimensions labeled. PL represents the pressure point length and ML represents the styloid process marker length.

In addition to varying the shape of the pressure point, the dimensions can also be varied. The force application surface of the pressure point itself, along with the side piece to line up with the styloid process (called the marker), can be shortened on the chamfered pressure point model. These dimensions are shown in FIG. 26.

A few different pressure points were modeled and Solidworks stress simulations were run to analyze the differences in maximum von mises stress and maximum displacement of the part. As seen in Table 1, we found that as the pressure point length and marker length decrease, the max displacement decreases as well.

TABLE 1

Table that displays the difference in in max displacement when the pressure point and marker lengths are changed

| Pressure Point Length (in) | Marker Length (in) | Max Stress (Von Mises) (Pa) | Max Displacement (mm) |
|---|---|---|---|
| 0.75 | 1.25 | $1.623 \times 10^7$ | $1.615 \times 10^{-2}$ |
| 0.5 | 1 | $1.595 \times 10^7$ | $1.484 \times 10^{-2}$ |
| 0.5 | 0.75 | $1.548 \times 10^7$ | $1.48 \times 10^{-2}$ |
| 0.25 | 0.75 | $1.697 \times 10^7$ | $1.399 \times 10^{-2}$ |
| 0.25 | 0.5 | $1.587 \times 10^7$ | $1.394 \times 10^{-2}$ |

These simulations were run with a force of 550 N per face. For example, at a pressure point length of 0.75 inches and a marker length of 1.25 inches, the maximum displacement is $1.615*10^{\wedge}-2$ mm. Meanwhile, when the pressure point length is 0.5 inches and the marker length is 1 inches, the max displacement is $1.484*10^{\wedge}-2$ mm. Finally, at a pressure point length of 0.25 inches and a marker length of 0.75 inches, the max displacement is $1.399*10^{\wedge}-2$ mm. The ideal pressure point dimensions were determined to be 0.5 in for the pressure point length with a 1 in long marker. The pressure point piece was shortened slightly to reduce the maximum stress and displacement values but was not shortened below 0.5 in order to allow for the skin on the wrist to compress without the supporting block of the pressure point to contact the wrist. The marker length was found to have a minimal effect on the stress and displacement values and was set to be one inch to conform to wrist geometry.

Material Reductions

Even radiolucent materials show up on certain images, such as the CT scan, to some extent. Since the volume of material in the imaging region is as thick as it is, variations to reduce material while maintaining strength can be considered. A few initial designs modeled were circular honeycombs, diagonal fins, cutouts in the part, and reducing thickness in the middle of the part.

Figure 27A:
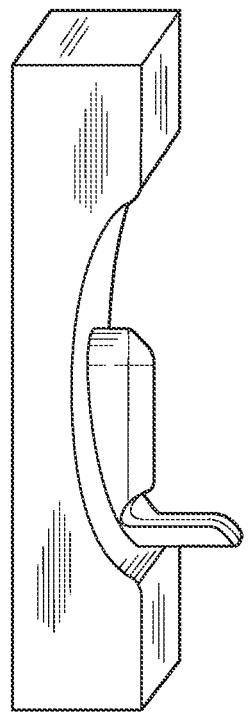
FIG. 27A, FIG. 27B, FIG. 27C, and FIG. 27D are exemplary CAD models of material reductions in the force application piece.
Figure 27B:
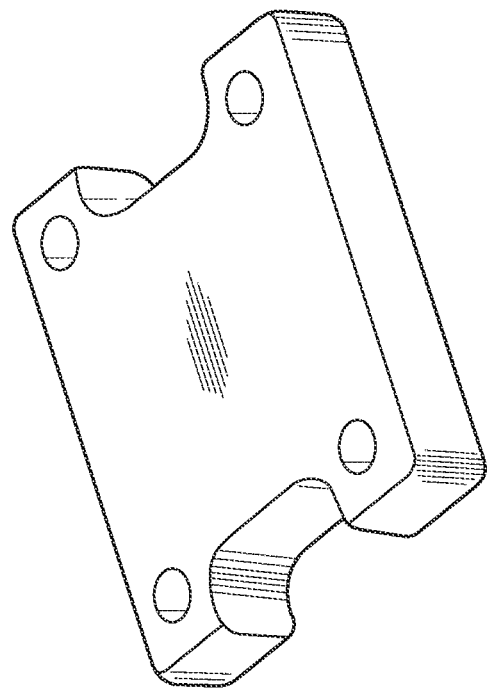

In some embodiments, the reduced thickness can be achieved by building the pressure point up into the support piece and leaving the maximum thickness around the rod holes, as shown in FIG. 27A. In some embodiments, material reduction can be achieved by inserting cutouts into the design, as shown in FIG. 27B. This reduced the material that the x-rays would have to image through when coming from an angle.

Figure 27C:
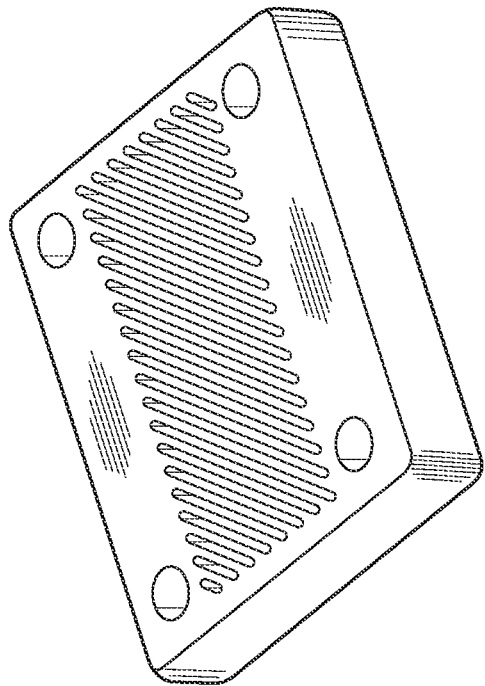
Figure 27D:
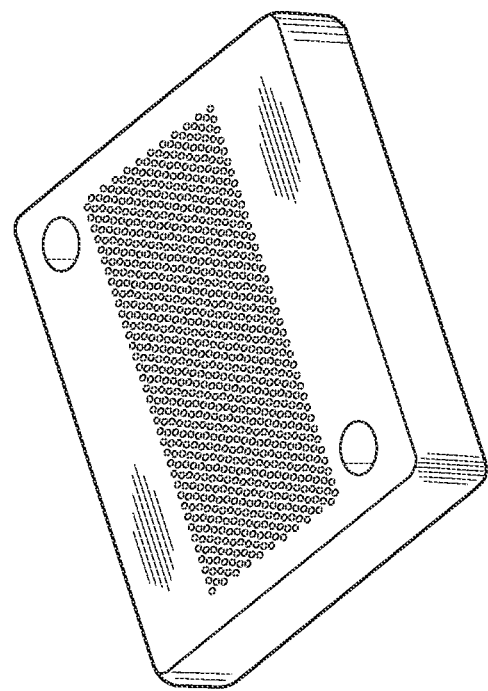

In some embodiments, another material reduction includes inserting fins. As shown in FIG. 27C, fins consist of material cutouts that run diagonal to the base. In some embodiments, honeycombing is another technique that can be implemented to reduce the amount of material. In honeycombing, circular and hexagonal cutouts run throughout the base of the material, as seen in FIG. 27D.

Table 2 displays differences in the volume of material in the imaging region, the max stress (in MPa), and the max displacement (in mm) for various material configurations. For this simulation, a force of 550 N was applied and Torlon 7130 was used as the material. Table 2 sorts the configurations that had the greatest maximum stress in order from highest to lowest. Some of the techniques to reduce material can be combined. For example, the circular honeycombs and the cutouts can be combined, or a circular honeycomb model can be used, which decreases the overall part thickness to 0.5 in.

TABLE 2

Table that displays the difference in max stress and max displacement when the material configuration is changed

| Reduced Material Configurations | Volume of Material in Imaging region | Max Stress (Von Mises) (MPa) | Max Displacement (mm) |
|---|---|---|---|
| Honeycomb + thinner | 3.94 | 1.09(10$^5$) | 4.49(10$^{-2}$) |
| Honeycomb + cutouts | 5.10 | 6.60 | 1.37(10$^{-2}$) |
| Built-in Pressure Point | 8.13 | 5.79 | 9.40(10$^{-3}$) |
| Honeycomb (Circular) | 6.88 | 3.705 × 10^6 | 7.894 (10$^{-3}$) |
| Fins | 6.69 | 3.42 | 8.50(10$^{-3}$) |
| Cutouts | 8.46 | 3.08 | 9.32(10$^{-3}$) |
| Default | 11.03 | 3.08 | 5.94(10$^{-3}$) |

As seen in Table 2, the default material configuration had the lowest maximum stress (of 3.08 MPa) when a force of 550 N was applied and the lowest maximum displacement value (of 5.94(10−3) mm) because it had the highest density of material. Although a lower maximum stress and displacement occurs in the default configuration, the model would also have the highest net cost and more importantly could cause the image to be unclear because of how thick the part is.

Out of the four models shown above, the circular honeycomb and the fins had considerably lower volumes than did the cutouts and the default model. The honeycomb model optimized the decreased volume of the material while still minimizing the displacement. Honeycombing was determined to be the optimal method of material reduction for this application.

A cellular solid is any solid, which is comprised of a repeating pattern of a cell. The cells share walls with their neighbouring cells. They can come in many shapes and in two-dimensional or three-dimensional patterns. Honeycombing is one of many types of cellular solids, which has a two-dimensional hexagonal pattern of close packed cells, as modeled in the honeycombs of a bee. Honeycombs are the simplest and most common of cellular solid patterns. Hexagonal honeycombs are known to minimize density of material without compromising the strength of the solid. Hexagonal honeycombs are proven to be stronger than other cell shapes, such as triangles or star-shapes. The effective elastic modulus of the cellular solid can be determined based upon the ratio of the length of the cell to the thickness of the material in between cells as shown in FIG. 28.

Figure 28:
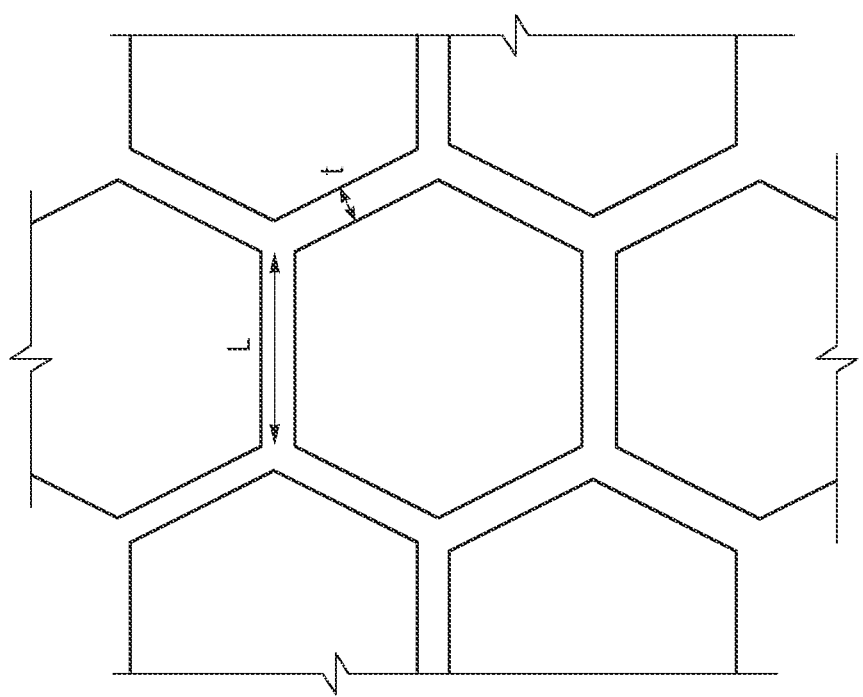
FIG. 28 is an image depicting the length of a cellular solid to thickness of the material in between cells.

The elastic modulus for a regular hexagon can be calculated using the formula:

$$E = (4/\sqrt{(3)})(E_s)(t^3/l^3)$$

where $E_s$ is the elastic modulus of the solid material, and t and l are the cell dimensions as shown in FIG. 28. Using these calculations, with a t:l ratio of 1, the elastic modulus of the cellular solid would increase. With a ratio of 1:2, the elastic modulus would be about 30 percent of the elastic modulus of the solid material.

The plastic stress of a honeycomb structure is the stress value at which the cells begin to collapse. This is calculated using the formula:

$$\sigma_{pl} = 2/3 (t^2/l^2) \sigma_y$$

where σy is the yield stress of the material. Because of the ⅔ fraction, a 1:1 ration for t:l will result in a plastic stress lower than the yield stress.

A hexagonal honeycombed model was determined to be ideal for material reduction and manufacturable via 3D printing.

Various devices can be evaluated relating to measuring the mechanical force that is applied. Different instruments can be used to measure the force, including a strain gauge based load cell, a piezoresistive force sensor, and a beam load cell.

Strain Gauge Based Load Cell

A strain gauge load cell contains a strain gauge, which is a device that uses electrical conductivity to measure the strain that occurs. A common type of strain gauge consists of rectangular pieces of foil with wires that lead to electrical cables.

The strain gauge is attached to the object of interest via a suitable adhesive. When an object, whose strain we are measuring, is deformed, the foil is deformed and this causes the foil's electrical resistance to change. Then, a wheatstone bridge is utilized to measure the resistance change, and a quantity known as the gauge factor relates the resistance change to the strain. The strain represents the change in length divided by the original length.

In a strain gauge load cell, a force is converted into a measurable electrical output. Additionally, in this load cell, strain gauges are bonded onto a structural member when a weight is applied, and four strain gauges are typically used in order to obtain sufficient sensitivity. When a weight is applied to the strain gauges, the strain changes the electrical resistance of the gauges in proportion to the load. Strain gauge-based load cells offer accuracies within 0.25% of the full scale (FS) measurement and are suitable for a variety of applications. These load cells can be used for static and dynamic measurement, involve no moving parts, and can accommodate a wide range of force measurements.

Piezoresistive Force Sensor

A piezoresistive force sensor measures force directly, in comparison to a load cell, which utilizes a strain gauge to measure the applied force. In this instrument, the applied force compresses two layers of a flexible, piezoresistive ink together. This compression results in a proportional change in electrical signal, and this device acts as a force sensing resistor in an electrical circuit. Furthermore, the resistance can be read by utilizing a multimeter and is inversely proportional to the applied force.

This type of sensing device is durable and can be used in a wide variety of environments. Furthermore, they are small and relatively low in terms of cost (around $20). These sensors can also be attached to many surfaces and allow for ease of integration. Comparing these sensors to strain gauge-based load cells, an exemplary piezoresistive force sensor offers an accuracy of +/−2.5% within the full-scale measurement. Additionally, calibration is also needed in this method, and piezoresistive force sensors usually are only able to measure forces up to approximately 100 N. Meanwhile, the amount of force that would need to be applied for an intermediately healed fracture is up to 550 N.

Beam Load Cell

Figure 29:
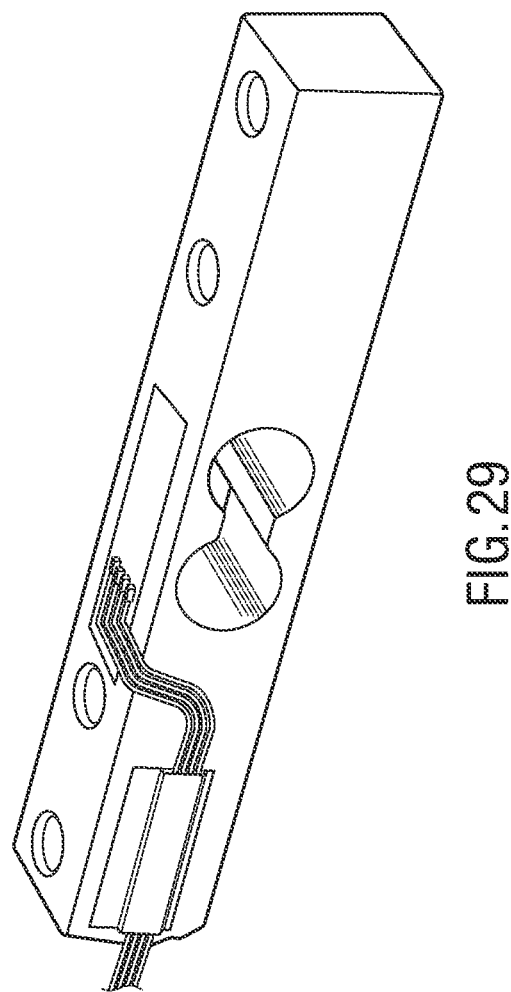
FIG. 29 is an image of a beam load cell.

Beam load cells are a type of strain gauge load cell that can convert an electrical signal to a measurable force. A beam load cell contains a metal spring element, which is deformed elastically when a weight acts upon it. This elastic deformation is converted into an electrical signal via a strain gauge, and FIG. 29 shows an image of an exemplary beam load cell.

Beam load cells can measure forces from several newtons up to approximately 2940 N, which is more than the required amount of 550 N. These load cells can offer a high accuracy of +/−0.030% within the full scale measurement and are relatively low in terms of cost. Beam load cells can be larger in comparison to strain gauge based load cells. For example, one beam load cell found online had dimensions of 1.57"×5.91"×1.38" in comparison to a strain gauge load cell, which had dimensions of 1.7"×1.5"×0.12". Beam load cells also require calibration.

Design Calculations

Various factors can be used to determine the ranges of force needed to produce displacements detectable by an imaging device, such as the HR-pQCT scanner (XtremeCT, Scanco, Switzerland) in a healing human distal radius.

In some embodiments, the minimum displacement detectable is defined as 82 microns, the voxel resolution of the micro CT scanner used. For example, the displacement can be twice this distance, 164 microns, to produce movement visible in at least two voxels, thus improving the sensitivity of the image to a displacement in the bone (due to increasing the ratio of displacement to resolution scale). The following calculations use a standard linear elastic solid model to calculate fracture displacement in a simplified human forearm model when subjected to external loading.

In this one-dimensional model, a spring with stiffness constant K is displaced by a distance ΔL due to the application of a force F.

Linear Elastic Spring Model:

$$F = K * \Delta L$$

Using simple stress analysis, the 2-dimensional model accounts for force distribution across cross-sectional areas of the bone and soft-tissue.

Stress Analysis Model:

$$F = \sigma * A = E * \varepsilon * A$$

Here, σ represents the stress (force divided by area), A is the cross-sectional area, E is the elastic modulus of the bone, and ε is the strain, which is defined as the change in length divided by the initial length.

Example 2

Figure 30:
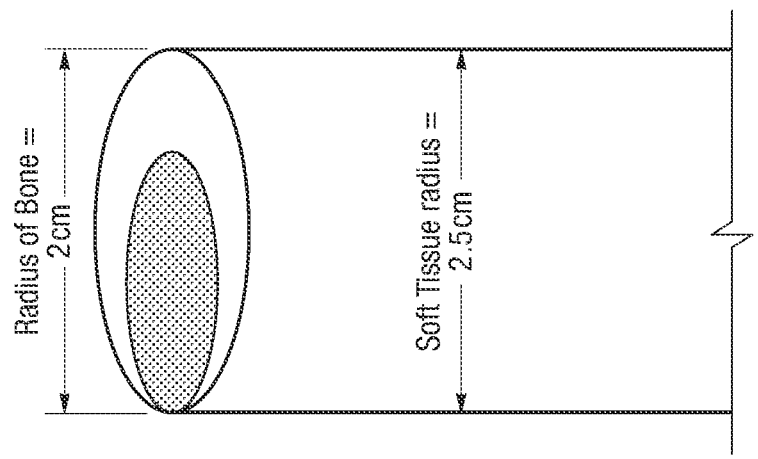
FIG. 30 is an image of radius of bone and soft tissue.

The following properties of bone are used in the calculation for Example 2: soft tissue radius is 2.5 cm, the radius of the bone is 2 cm, and bone callus radius is 2.25 cm. An image of the properties used in the calculation is shown in FIG. 30.

These calculations were performed iteratively for a healing complete fracture using the different elastic modulus values known for various healing stages.

Fresh, Complete Break:

$E = 1.23 \times 10^{\wedge} Pa - 3.15 \times 10^{\wedge}3$ Pa for that of skin/muscle:

$F = <1$ N

Early Union:

$E = 5\text{-}10$ MPa→Woven Bone $F = 7\text{-}15$ N

Intermediate Healing:

$E = 100\text{-}500$ MPa $F = 100\text{-}550$ N

Good Union:

$E = 15\text{-}20$ GPa $F = 16\text{-}22$ kN

It is shown that in the first three stages the force needed to displace the fracture increases by six orders of magnitude. The device will need to be able to apply a force from a few Newtons to around 550 N. It is possible that in the later stages of healing, when the bone is well joined, that the fracture will not be able to be displaced without injuring soft tissue. At this stage, the bone will no longer be considered at risk for healing complications, and will likely not need further mechanical testing for appropriate treatment.

Example 3

The following calculations were completed in order to determine the amount of force that would need to be applied to the distal radius. These calculations assume that the bone is a linear elastic, isotropic solid, which means that it fully recovers all deformation due to loading and has the same physical properties when measured in different directions. Additionally, the bone was modeled as a circular hollow beam in order to solve for the force. The equation for the deflection at any point is:

$$d = \frac{Fx^2}{6EI}(3L - x).$$

Figure 31:
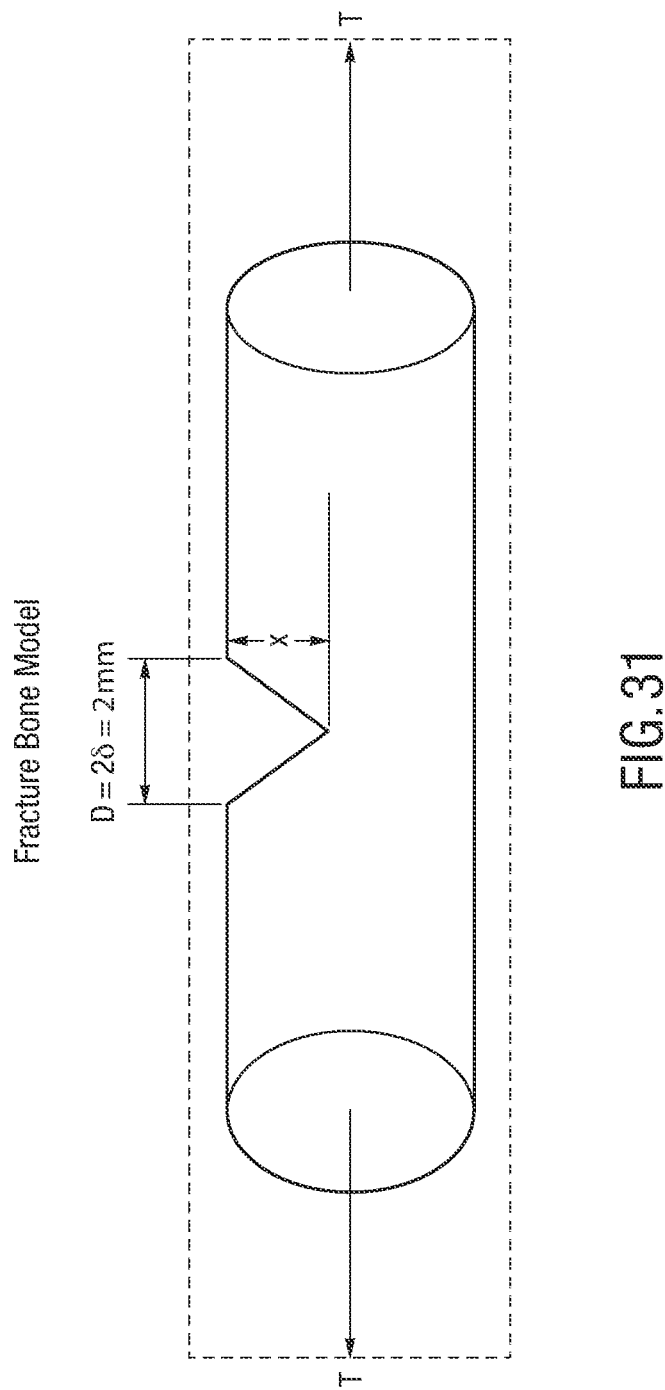
FIG. 31 is a schematic of the tensile force (T) that is applied to a fractured bone, with the deflection (d) being equal to 2 mm, and x represents the length of the fractured bone.

In this equation, F represents the force acting on the bone, L represents the length of the bone, E represents the bone's modulus of elasticity, and I represents the area moment of inertia of the bone's cross section. As seen in FIG. 31, a tensile force can be applied to both sides of the bone. Therefore, F is equal to 2T, in which T represents the tensile load acting on the bone. It is assumed that the displacement is small such that the angle of the broken surfaces is negligible. By substituting 2T into the equation, and by setting L=x, the equation becomes:

$$d = \frac{(2T) * x^2}{6EI}(3x - x).$$

Solving for the tensile force, the equation becomes:

$$T = \frac{(3d)EI}{2x^3}.$$

The area moment of inertia is a half circle about the flat portion, and has the following equation:

$$I = \frac{\pi r^4}{8}$$

In this equation, r represents the radius of the distal radius and by plugging in the area moment of inertia into the deflection equation, the formula reduces $$T = \frac{(3d)E(\pi r^4)}{16x^3}$$

Through background research, the team has found that the radius r of the distal radius is approximately r=1.59 cm or 0.0159 m, the modulus of the healthy bone is approximately E=10.5 GPa or 10,500 ($10^6$) Pa, and the maximum deflection that can be applied to bone is approximately d=2 mm. By substituting these values into the equation $$T = \frac{(3d)E(\pi r^4)}{16x^3}$$

it is found that the tensile force is approximately T=197($10^3$) N or 197 kN.

This equation can be solved for the cases in which the deflection d=1 mm and d=0.165 mm (165 μm).

For the case in which d=1 mm, the required force would be approximately 98 kN.

For the case in which d=165 μm, the required force would be approximately 16 kN.

Table 3 shows a summary of the results that were found via the calculations, and the amount of force needed to displace a healthy bone (with an incomplete fracture) is in the kN range.

TABLE 3

Summary of the Tensile Forces required to displace healthy bone.

| Deflection | Tensile Force Required |
| --- | --- |
| 0.165 mm (165 μm) | 16 kN |
| 1 mm | 98 kN |
| 2 mm | 197 kN |

It can be noted that it is likely not possible to apply the magnitude of force necessary to displace an incomplete fracture through the tensile method because these forces have to be applied through the overlying soft tissue, which is likely to be damaged by this level of force.

The bending stress design (in comparison to the tension design) can displace unusual fracture geometries and has mechanical advantage from the bending force application geometry; this mechanical advantage allows for higher internal bone forces with lower external soft tissue forces at the force application points.

Design Conclusions

TABLE 4

Pros of Tension and Bending Designs

| | Pros |
| --- | --- |
| Bending | Simpler design |
| | Less moving parts |
| | Offers a mechanical advantage |
| | Left/right compatibility |
| | More Affordable |
| Tension | Worm screw and operation is outside of field of view and more easily accessible |
| | Different L/R accessories |

As seen in Table 4, the bending design involves fewer moving parts and is much simpler in comparison to the tension design. This can improve the device's repeatability and ability to remain rigid when a mechanical force is applied. The bending design also offers a mechanical advantage via 3-point bending, allows for easy right/left (R/L) changeover, and is more affordable. A key limitation of the bending design is that the patient will need to remove his/her cast in order to use the device, and it can be difficult to adjust loading while inside the scanner.

The tension design also allows for R/L compatibility, the ability to adjust the loading easily, and the ability to leave on the cast. The drawbacks to the tension design include difficulty in gripping the hand and elbow mechanisms and relative design complexity that involves more moving parts. This can affect the ability of the device to apply a repeatable load and to remain stable during force application.

Some slight design updates can include a less angular design. This can improve comfort and maximize the use of the scanner's cylindrical field of view. Velcro strapping will be added for arm security, and the load cell for force measurements. The geometry of the pressure point can be designed such that the force is spread over a suitable area on the wrist and not directly to the ulna.

Optimization

To select the loading type and mechanisms, several of requirements can be taken into consideration including but not limited to repeatability, ability to fit within an imaging device such as a CT scanner, range of force that the design is able to apply, ease of use, and ergonomics. In some embodiments, a 3-point bending design can be used as this device can apply a suitable and repeatable mechanical load.

For the tension design gripping mechanisms, components can be used that are able to withstand higher forces and able to remain secure while a mechanical load is applied. Several key requirements taken into consideration regarding the load cell, including but not limited to space constraints, range of force, accuracy, and ease of use. The load cell can be selected because it is accurate and can measure close to the upper portion for intermediate healing (550 N). It is also able to fit in a limited space and is relatively easy to use. Another design consideration evaluated is the type of frame the device has. For the frame, we considered using bottom supports, single side supports, or a full cage support. In some embodiments, bottom supports can be used because they can fit well within the space constraints and it is the most affordable option in comparison to other types of frames. While a full cage support does offer more rigidity, this design will likely not be feasible due to space constraints inside the scanner.

The updated three-point bending design can be used as an effective method of applying the displacement load. Various materials can be chosen based upon radiolucency, cost effectiveness, and the ability to remain still when a mechanical load is applied. For example, PLA with carbon fiber reinforcement can be used, which is a radiolucent and thermoplastic material. This material can be environmentally friendly, available at a low to moderate cost, and offer high flexural strength and reliable performance. A printer that can print carbon fiber along with traditional filaments became available however, and it was decided to use this method with threaded inserts to produce the first full prototype.

Bearing Ratio Considerations

Figure 32:
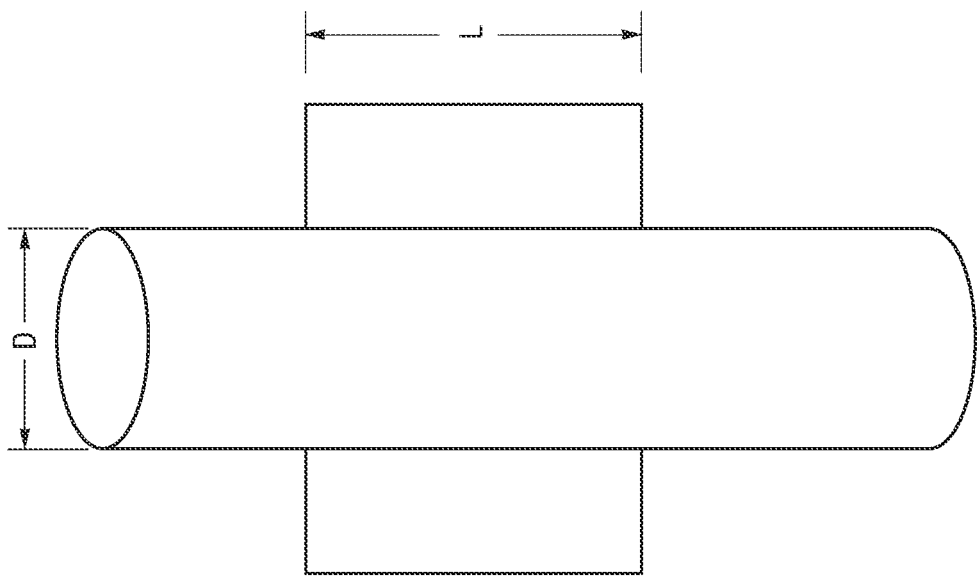
FIG. 32 illustrates a bearing ratio of a sliding mechanism.

Bearing ratio (BR) is the ratio of the total length of the slide bearing to the diameter of slide, as shown in FIG. 32. In some embodiments, a bearing ratio of >1.5 is required for smooth sliding at all speeds, and a bearing ratio of <1 will induce mechanism binding even at slow speeds. For this device, bearing ratio represents the ratio of the distance between rod supports over the maximum rod separation. In some embodiments, D=3.75, L=5.5 in (entire rod length) which cannot exceed ~6.5 in due to scanner dimensions leading to a BR=1.47. This is slightly under the ideal 1.5, but not a problem due to the slow speeds indicated for this application.

A design principle from kinematics known as the bearing ratio for sliding parts may cause problems with the smooth translation of the loading mechanism. The bearing ratio of the design was assessed, determined to be within the acceptable limit, and sliding guide rods were added to the loading mechanism for improved stability.

Drive Mechanism Resolution

The initial loading mechanism calibration tests indicated that once secure compression was achieved, it took only 7/24 of a turn, about 105, of the ½ with 13 inch threaded rods to produce the maximum force rating of the load cell of approximately 550 N. This means that there is very little control in the loading range (in terms of Newtons per degree) that is available to the technician operating the device in a clinical setting. Lack of control of the loading mechanism could lead to inappropriate or damaging loads on a patient, so this problem was corrected.

Assuming a fully rigid, non-conforming mechanism, and complete force transfer, the following calculations were made to quantify this effect in engineering terms presented in Table 5.

TABLE 5

Improved Thread Pitch Force Resolution Calculations

|  | ½-13 thread | ½-40 thread |
| --- | --- | --- |
| Number of turns total range | 0.29 | 11.67 |
| Vertical displacement per turn | 1/13 in | 1/40 in |
| Average force per degree turn | 21.9 N/deg | 0.07 N/deg |
|  |  | >300x higher resolution |

At 13 tpi (turns per inch), each full turn corresponds to 1/13 of an inch of vertical displacement in the loading mechanism, which is equivalent to approximately 0.076 inches/turn so 0.2917 inches corresponds to an average of 21.9 N/degrees of rotation. At 40 tpi however, 0.2917 inches corresponds to 0.07 N/degrees of rotation, a more than 300 times increase in resolution.

It can be noted that this curve is best fit as a power curve, so averages are used to describe the whole range in a comparative fashion. Additionally, the mechanism is calibrated without a wrist phantom, and therefore deflection can attributed only to the loading mechanism. It is important to note that the deflection is not representative of a human, who is expected to exhibit greater compliance. The calculations above display a significant improvement in drive distance resolution.

Materials that can be used to make the device include but are not limited to the hand brace and carbon fiber reinforced Onyx. The plastic material, Onyx, is recyclable by shredding and washing the material, and then turning the material into a granulate (which will be ready to be used again). Additionally, carbon-fibre polymer composites (such as Onyx) have been shown to be recyclable through other techniques. For example, one method that can be implemented involves using supercritical fluids to separate the polymer matrix and carbon fibers. This process can degrade the resin into lower molecular weight compounds. The tensile properties of the fibers have been shown to retain their original tensile strength. In addition, the fibers can remain undamaged and retain their original morphology.

In some embodiments, the device can be formed using 3D printing as the manufacturing technique. In some embodiments, injection molding can be used to form the device. 3D printing allows for quicker manufacturing time and lower production costs.

Sustainability covers many aspects of this device. One aspect was the material that would be utilized during production, and in some embodiments Carbon Fiber reinforced PLA for 3D printing can be used. This plastic can be more sustainable in comparison to traditional plastics, which are petroleum based. For example, producing PLA results in a reduction of 68% greenhouse gas emissions versus petroleum based plastics. Furthermore, it requires 65% less energy to produce PLA in comparison to conventional plastics.

Due to its superior processability with carbon fiber, CF filled nylon can be used. Nylon is recyclable and low cost, while carbon fiber is inert to the environment during post processing.

Device Manufacturing

The loading region of the base, pressure point piece and top piece of the device will most likely be manufactured via 3D printing using Onyx, a filament made of carbon fiber and nylon. This printer will allow for the carbon fiber to be laid in varying amounts and orientations, which increases the strength of the part while maintaining radiolucency.

Device Operation

The device is operated by turning the crank on the side of the proximal end of the base. This connects via a short gear train to a push pull pulley system. As the proximal pulley is turned, one side of the chord is pushed towards the distal pulley, and the other side is pulled back causing rotation in the distal pulleys. As the distal pulleys are rotated together, the pressure point piece is moved linearly downwards, applying a compressive force to the sagittal surface of the wrist. As the compressive force is applied to the wrist, the heel of the hand and distal end of the forearm experience opposing reaction forces from the base piece, causing the 3 point bending. An image will be taken with the device in the loaded state so that the displacement of the bone ends can be seen. Once a displacement of 2 mm is achieved, the force used to reach this displacement will fall into a category of wrist fracture healing ranges. These ranges were determined through calculation of the stiffness of the bone with the given displacement and applied force.

In some embodiments, the device can be formed from carbon fiber reinforced polycarbonate through injection molding. An injection molded part can increase the strength because the carbon fiber reinforcement in these plastics are in webs as opposed to the short chopped fibers of 3D printing filaments. Increasing the strength through injection molding can also allow for a reduction in the amount of material in the imaging section through honeycombing. Honeycombing is not recommended for 3D printed parts because it would likely decrease the strength significantly due to the layered nature of the prints.

Some other design aspects which can be incorporated into various embodiments of the device include a quick release system and another embodiment of a force adjustment knob. A quick release system can allow for the loading to be immediately released back to zero instead of having to slowly decrease the load by turning the pulley or other mechanism in the opposite direction. Another embodiment of a force adjustment knob can be located on the side of the device instead of the bottom for an easier reach for a user, such as a physician.

Example 4

Distal radius fractures, specifically Colles' fractures are the most common bone injury in adults, with the majority occurring in postmenopausal women. Often these fractures result in painful healing defects including non-union and delayed union, leading to extended treatment and even surgery. Currently, there is no clinical method to quantify the extent of bone healing beyond the limited capabilities of standard x-rays. The goal of this project is to develop a device which can determine the strength of the healing fracture for both clinical and research applications. This is achieved by applying a known bending load to the distal radius and measuring the displacement of the bone in HR-pQCT images. The elastic modulus of the callus material can then be calculated and correlated to a stage of bone healing. The device created was manufactured via 3D printing with carbon fiber reinforced Onyx (nylon). Validation of device performance was performed using cadaver wrists models.

Distal radius fractures are the most common bone fracture, accounting for 8-15% of all bone injuries in adults. These fractures typically occur on the distal end of the long bone, one to two inches proximal of the radiocarpal joint. The most common type of distal radius fracture is the Colles' fracture; a transverse fracture of the metaphyseal region typically caused by falling forwards onto the outstretched palm from standing. Seventy percent of Colles' fractures occur in postmenopausal women who are prone to fragility fractures resulting from both decreased balance, and lower bone density. Because of the decreased bone density, the low-energy impact of an attempt to break the fall applies sufficient force to yield the bone and cause fracture. The average payment for Medicare patients with distal radius fracture was 1,983 dollars in 2007.

Bone healing time is typically six to eight weeks in a healthy individual. Complications occur in up to 80% of these fractures. In osteoporatic individuals, healing time is increased by an unknown amount. Due to a physician's inability to determine exact extent of healing, Colles' fracture casts are often removed prematurely when the bone has not been fully healed (known as delayed union). Alternatively, an improperly or incompletely healed bone may be discovered when there is continuing pain after removal of the cast. Another major healing defect is non-union, which typically occurs with wide separation between bone ends. Both complications fail to reestablish the rigidity and strength necessary for proper function. This leads to pain, risk of fracture re-injury, and other healing complications. Both delayed and improper healing can result in further treatment up to and including surgery to correct the healing defect resulting in extended treatment times and decreased quality of patient outcomes.

Detecting healing defects earlier can help to prevent premature cast removal in patients with distal radius fractures. This can be accomplished through the design and manufacture of a device which applies a known mechanical load to the fracture to produce a small, safe displacement, which is measurable in an imaging device, such as a HR-pQCT scanner. Bone strain can then be measured through standard elastic displacement models commonly used in materials engineering applications. Stiffness is then correlated to a particular stage of the healing process with reference to established healing bone mechanics. Bone strain measurement will also enable the quantification of strength recovery in the fracture callus.

A device can be used to allow physicians to quantify the extent of strength recovery and bone healing in distal radius (wrist) fractures, which occur primarily in postmenopausal women, to permit early detection of common healing complications, and inform treatment to improve patient outcomes. The device will be used in a HR-pQCT scanner in order to permit the calculation of callus stiffness by using a known load to produce a visible displacement.

A two millimeter displacement of bone was determined through literature review to be safe for the healing bone, and visible on the scan images. The literature shows that the bone callus of a distal radius fracture will be in the range of 1-3 kPa for no healing, 5-10 MPa for early union, 100-500 MPa for intermediate healing and 15-20 GPa for complete healing. It was determined that the maximum force needed to reach the upper end of the intermediate range of healing would be 500 N. Beyond this, it is assumed that the bone is in stable union and is expected to fully recover; with further testing unnecessary.

Loading the bone in bending produces the necessary displacement at lower force levels than other loading methods. After preliminary design work and testing was completed, it was determined tension is not feasible due to the difficulty of securing the hand and elbow, magnitude of through-joint loading, and anatomic variation.

The forearm is secured palm down onto a padded base, which serves as the two support points for the 3 point bending method, using hook and loop straps. The moving piece with a pressure point protrusion is pressed downwards onto the wrist as the third point to apply the bending loading as shown in FIG. 1.

After consideration of several loading mechanisms, a non-backdriveable screw drive was selected. This consists of two ½-20 threaded steel rods. The rods are placed outside of the device's imaging region, allowing them to be metal and obtained commercially without interrupting the CT image. The loading mechanism was tested to determine the necessary forces were obtainable using a preliminary model and a button load cell.

As the rods are turned by the user via a nylon pulley system on the base of the device, the protruding point on the top piece is driven downwards to apply increasing force to the radius. A strain gauge located on a non-threaded surface of one of the rods is calibrated to indicate the tension in the rod. Twice this tension represents the total applied force.

Both benchtop cadaver arm testing were used to validate the mechanical and clinical functionality of the device. A fracture was created in a cadaver radius by sawing the bone in half. The device was imaged with a phantom and QCT analysis compared to determine image clarity.

Major aspects of the device design which were validated were load applied, pain levels, radiolucency, and fracture displacement.

The loading range of the mechanism verified through testing with a calibrated load cell. The device can apply 0-700 N, with a resolution of (force/in/degree) well beyond the needed force.

A major design constraint is that the device be sufficiently comfortable for patients to remain still for the duration of the 2-5 minute scan to prevent motion artifact in the image. Self-experimentation within the team was used to assess discomfort of pressure point geometry with varying loads applied to the wrist. Pain was rated on the Self-Assessed Pain Scale of 1-10 and found to be tolerable within the needed loading range.

Radiolucency of the device was ensured through careful material selection and imaging of the device with avian bone revealing satisfactory clarity in the radiolucent region.

The device can be designed to apply loading sufficient to produce detectable displacement in healing distal radius fractures for use in imaging device, including HR-pQCT imaging. Bone stiffness and therefore extent of healing can be calculated using this method. Patient comfort can be achieved through device geometry and padding.

The device permits the quantitative measurement of healing distal radius fractures in conjunction with imaging, such as HR-pQCT imaging. This device can quantify healing extent in distal radius fractures in an at-risk population for healing complications, and can improve the standard of care and patient outcomes for distal radius fractures.

Figure 33:
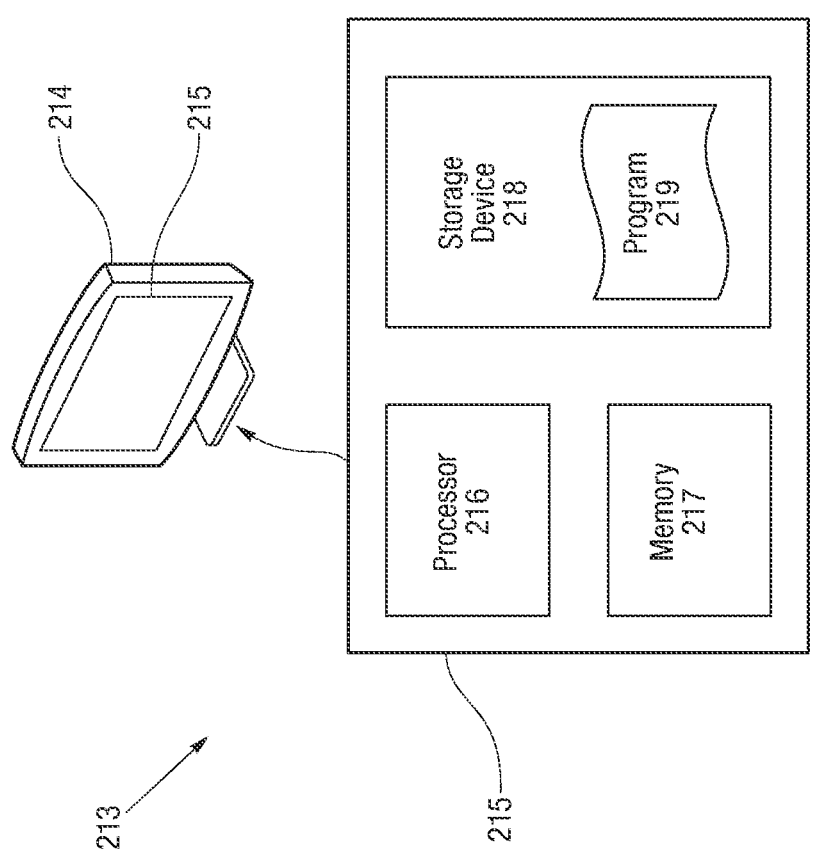
FIG. 33 is a diagram showing an exemplary computer system suitable for use with the methods and systems of the present disclosure.

FIG. 33 shows, by way of example, a diagram of a typical processing architecture, which may be used in connection with the methods and systems of the present disclosure. A computer processing device 213 can be coupled to display 214 for graphical output. Processor 215 can be a processor 216 capable of executing software. Typical examples can be computer processors (such as Intel® or AMD® processors), ASICs, microprocessors, and the like. Processor 216 can be coupled to memory 217, which can be typically a volatile RAM memory for storing instructions and data while processor 216 executes. Computer processor 216 may also be coupled to storage device 218, which can be a non-volatile storage medium, such as a hard drive, FLASH drive, tape drive, DVDROM, or similar device. Although not shown, computer processing device 213 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 213. Computer processor 216 may also be coupled to other type of computer-readable media, including, but are not limited to, an electronic, optical, magnetic, or other storage or transmission device capable of providing a processor, such as the processor 216, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 219 can be a computer program or computer readable code containing instructions and/or data, and can be stored on storage device 208. The instructions may comprise code from any computer-programming language, including, for example, C, C++, C#, Visual Basic, Java, Python, Perl, and JavaScript. In a typical scenario, processor 216 may load some or all of the instructions and/or data of program 219 into memory 217 for execution. Program 219 can be any computer program or process including, but not limited to a web browser, a browser application, an address registration process, an application 142, or any other computer application or process. Program 219 may include various instructions and subroutines, which, when loaded into memory 217 and executed by processor 216 cause processor 216 to perform various operations, some or all of which may effectuate the methods for managing medical care disclosed herein. Program 219 may be stored on any type of non-transitory computer readable medium, such as, without limitation, hard drive, removable drive, CD, DVD or any other type of computer-readable media.

Certain aspects of the present disclosure include process steps and instructions described herein in the form of an algorithm. It should be noted that the process steps and instructions of the present disclosure could be embodied in software, firmware or hardware, and when embodied in software, could be downloaded to reside on and be operated from different platforms used by a variety of operating systems. The disclosure can also be in a computer program product which can be executed on a computing system.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a tangible computer-readable (or machine-readable) storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. In some embodiments, the computer is connected to a display to display the images generated by the instant methods.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description. In addition, the present disclosure is not described with reference to any particular programming language. It will be appreciated that a variety of programming languages may be used to implement the teachings of the present disclosure as described herein, and any references to specific languages are provided for disclosure of enablement and best mode of the present disclosure.

As will be understood by those familiar with the art, the invention may be embodied in other specific forms without departing from the spirit or essential characteristics thereof. Likewise, the particular naming and division of the modules, features, attributes, methodologies, managers and other aspects are not mandatory or significant, and the mechanisms that implement the invention or its features may have different names, divisions and/or formats. Furthermore, as will be apparent to one of ordinary skill in the relevant art, the modules, features, attributes, methodologies, managers and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A fracture testing system comprising:
   an imaging device configured to image a bone fracture in a bone before and after the application of a force thereto;
   a fracture testing device comprising:
      a base configured to receive an arm of a patient having the bone fracture;
      a force application platform, wherein the force application platform is moveable relative to the base along one or more guide rods;
      an inflatable force applicator disposed on a side of the force application platform facing the base, such that the force applicator can be positioned in contact with the arm of the patient;
      a pump in communication with the force applicator so that the pump can inflate the force applicator to a desired pressure to apply a desired force on the bone fracture,
   wherein the fracture testing device is placed relative to the imaging device to enable the imaging device to image a displacement of the bone fracture.

2. The fracture testing system of claim 1 further comprising a strain gauge or load cell to measure a strain on the bone.

3. The fracture testing system of claim 1 wherein the force application platform is configured to allow the bone to bend to cause a displacement of the fracture.

4. The fracture testing system of claim 3 wherein the displacement is between about 82 microns and about 500 microns.

5. The fracture testing system of claim 3 wherein the displacement is between about 164 microns and about 250 microns.

6. The fracture testing system of claim 1 wherein the imaging device is High Resolution Peripheral Quantitative Computed Tomography (HR-pQCT).

* * * * *